US010278695B2

(12) United States Patent
Milo

(10) Patent No.: US 10,278,695 B2
(45) Date of Patent: May 7, 2019

(54) SURGICAL STAPLER

(71) Applicant: QuickRing Medical Technologies Ltd., Haifa (IL)

(72) Inventor: Simcha Milo, Haifa (IL)

(*) Notice: Subject to any disclaimer, the term of this patent is extended or adjusted under 35 U.S.C. 154(b) by 280 days.

(21) Appl. No.: 15/034,471

(22) PCT Filed: Nov. 4, 2014

(86) PCT No.: PCT/IB2014/002992
§ 371 (c)(1),
(2) Date: May 4, 2016

(87) PCT Pub. No.: WO2015/063609
PCT Pub. Date: May 7, 2015

(65) Prior Publication Data
US 2016/0262744 A1   Sep. 15, 2016

Related U.S. Application Data

(60) Provisional application No. 61/899,654, filed on Nov. 4, 2013.

(51) Int. Cl.
*A61B 17/10* (2006.01)
*A61B 17/04* (2006.01)
(Continued)

(52) U.S. Cl.
CPC ........ *A61B 17/068* (2013.01); *A61B 17/0644* (2013.01); *A61B 17/0682* (2013.01);
(Continued)

(58) Field of Classification Search
CPC ................ A61B 17/068; A61B 17/105; A61B 2017/00477; A61B 2090/0811; A61B 2017/00473; A61B 2017/2919
(Continued)

(56) References Cited

U.S. PATENT DOCUMENTS 4,610,383 A * 9/1986 Rothfuss .......... A61B 17/07207
227/176.1
4,648,542 A   3/1987 Fox et al.
(Continued)

FOREIGN PATENT DOCUMENTS

EP         0648476        1/1998
JP       2004534591      11/2004
(Continued)

OTHER PUBLICATIONS

Extended European Search Report, dated Jun. 20, 2017 for European Application No. 14858128.3 (8 pgs.).
(Continued)

*Primary Examiner* — Robert Long
(74) *Attorney, Agent, or Firm* — Fitch, Even, Tabin & Flannery LLP

(57) ABSTRACT

A surgical stapler includes a control handle having a forward-extending barrel and a stapling device at the distal end of the barrel, where the stapling device has a stapling head part, a stapler body part, and a hinge connection therebetween such that the stapling head part is pivotable relative to the barrel. The stapling head part has a holder region, opposite the hinge connection, configured for holding a surgical staple during positioning and implanting the staple. The proximal end portion of the stapling head part can be pivoted outwardly relative to the barrel to at least about 15° from an at rest position, juxtaposed with the stapler body part, to an active position for implantation of a staple into tissue in a generally proximal direction toward the control handle.

20 Claims, 31 Drawing Sheets

(51) Int. Cl.
  *A61B 17/068* (2006.01)
  *A61B 17/064* (2006.01)
  *A61B 17/00* (2006.01)
  *A61B 17/34* (2006.01)
  *A61B 90/00* (2016.01)

(52) U.S. Cl.
  CPC ........ *A61B 17/105* (2013.01); *A61B 17/3421* (2013.01); *A61B 2017/00243* (2013.01); *A61B 2017/00783* (2013.01); *A61B 2017/0645* (2013.01); *A61B 2017/3425* (2013.01); *A61B 2090/034* (2016.02); *A61B 2090/036* (2016.02); *A61B 2090/08021* (2016.02)

(58) Field of Classification Search
  USPC ............. 227/175.1–182.1; 606/75, 138–139, 606/142–143, 219, 300
  See application file for complete search history.

(56) References Cited

U.S. PATENT DOCUMENTS

| | | | |
|---|---|---|---|
| 5,042,707 A | | 8/1991 | Taheri |
| 5,431,323 A | * | 7/1995 | Smith ................ A61B 17/0682 227/177.1 |
| 5,443,475 A | * | 8/1995 | Auerbach .......... A61B 17/1608 600/564 |
| 5,478,003 A | | 12/1995 | Green |
| 5,571,116 A | | 11/1996 | Bolanos et al. |
| 5,571,131 A | * | 11/1996 | Ek ..................... A61B 17/1608 606/167 |
| 5,725,554 A | | 3/1998 | Simon et al. |
| 5,891,160 A | | 4/1999 | Williamson |
| 6,312,447 B1 | | 11/2001 | Grimes |
| 6,482,224 B1 | | 11/2002 | Michler et al. |
| 6,575,971 B2 | | 6/2003 | Hauck et al. |
| 6,840,246 B2 | | 1/2005 | Downing |
| 6,921,407 B2 | | 7/2005 | Nguyen et al. |
| 7,278,563 B1 | * | 10/2007 | Green ............. A61B 17/07207 227/176.1 |
| 7,509,959 B2 | | 3/2009 | Oz et al. |
| 7,588,177 B2 | * | 9/2009 | Racenet ............... A61B 17/068 227/181.1 |
| 7,735,703 B2 | | 6/2010 | Morgan et al. |
| 7,938,827 B2 | | 5/2011 | Hauck et al. |
| 8,157,719 B1 | | 4/2012 | Ainsworth et al. |
| 8,167,905 B2 | | 5/2012 | Michler et al. |
| 8,292,147 B2 | | 10/2012 | Viola |
| 8,308,725 B2 | * | 11/2012 | Bell ................... A61B 17/3201 606/205 |
| 8,393,517 B2 | | 3/2013 | Milo |
| 8,475,491 B2 | | 7/2013 | Milo |
| 9,724,096 B2 | * | 8/2017 | Thompson ....... A61B 17/07207 |
| 9,936,953 B2 | * | 4/2018 | Thompson ....... A61B 17/07207 |
| 2001/0049469 A1 | | 12/2001 | Kortenbach |
| 2003/0125734 A1 | * | 7/2003 | Mollenauer ...... A61B 17/07207 606/51 |
| 2003/0220657 A1 | | 11/2003 | Adams |
| 2003/0220660 A1 | | 11/2003 | Kortenbach et al. |
| 2004/0059354 A1 | | 3/2004 | Smith |
| 2004/0193190 A1 | | 9/2004 | Liddicoat |
| 2005/0006432 A1 | * | 1/2005 | Racenet .......... A61B 17/07207 227/176.1 |
| 2005/0113832 A1 | | 5/2005 | Molz, IV |
| 2005/0149014 A1 | | 7/2005 | Hauck |
| 2005/0203547 A1 | * | 9/2005 | Weller ................ A61B 17/072 606/139 |
| 2005/0256533 A1 | | 11/2005 | Roth |
| 2006/0151568 A1 | * | 7/2006 | Weller .............. A61B 17/0218 227/175.1 |
| 2007/0023477 A1 | * | 2/2007 | Whitman ......... A61B 17/07207 227/175.1 |
| 2007/0027469 A1 | * | 2/2007 | Smith .............. A61B 17/07207 606/205 |
| 2007/0114261 A1 | | 5/2007 | Ortiz et al. |
| 2008/0147116 A1 | | 6/2008 | Smith |
| 2008/0149685 A1 | | 6/2008 | Smith et al. |
| 2009/0105535 A1 | | 4/2009 | Green et al. |
| 2009/0125038 A1 | | 5/2009 | Ewers et al. |
| 2009/0236388 A1 | | 9/2009 | Cole et al. |
| 2009/0250501 A1 | | 10/2009 | Sonnenschein et al. |
| 2010/0213240 A1 | * | 8/2010 | Kostrzewski ........ A61B 17/072 227/180.1 |
| 2011/0264208 A1 | | 10/2011 | Duffy et al. |
| 2013/0020372 A1 | | 1/2013 | Jankowski |
| 2013/0153625 A1 | * | 6/2013 | Felder ................. A61B 17/072 227/175.1 |
| 2013/0153642 A1 | * | 6/2013 | Felder .............. A61B 17/07207 227/181.1 |
| 2013/0221060 A1 | | 8/2013 | Racenet |
| 2014/0231489 A1 | * | 8/2014 | Balbierz .............. A61B 17/068 227/178.1 |
| 2015/0048141 A1 | * | 2/2015 | Felder .................... A61B 17/11 227/179.1 |
| 2017/0095251 A1 | * | 4/2017 | Thompson ....... A61B 17/07207 |
| 2018/0199941 A1 | * | 7/2018 | Thompson ....... A61B 17/07207 |

FOREIGN PATENT DOCUMENTS

| | | |
|---|---|---|
| JP | 2005523106 | 8/2005 |
| WO | 2015063609 | 5/2015 |

OTHER PUBLICATIONS

International Search Report, dated Jul. 6, 2016 for International Application No. PCT/IB2015/002365 (4 pgs.).
Written Opinion of the International Searching Authority, dated Jul. 6, 2016 for International Application No. PCT/IB2015/002365 (6 pgs.).
International Search Report dated Jul. 30, 2015 for International Application No. PCT/IB2014/002992 (4 pgs.).
Written Opinion of the International Search Authority for International Application No. PCT/IB2014/002992 (6 pgs.).
English translation of Chinese Patent Office First Office Action, dated Aug. 14, 2018 for Chinese Application No. 2014800721249 (8 pgs.).
English translation of Japanese Patent Office Notice of Reasons for Rejection, dated Aug. 15, 2018 for Japanese Application No. 2016-552708 (3 pgs.).
European Patent Office Examination Report, dated Jun. 4, 2018 for European Application No. 14858128.3 (4 pgs.).

\* cited by examiner

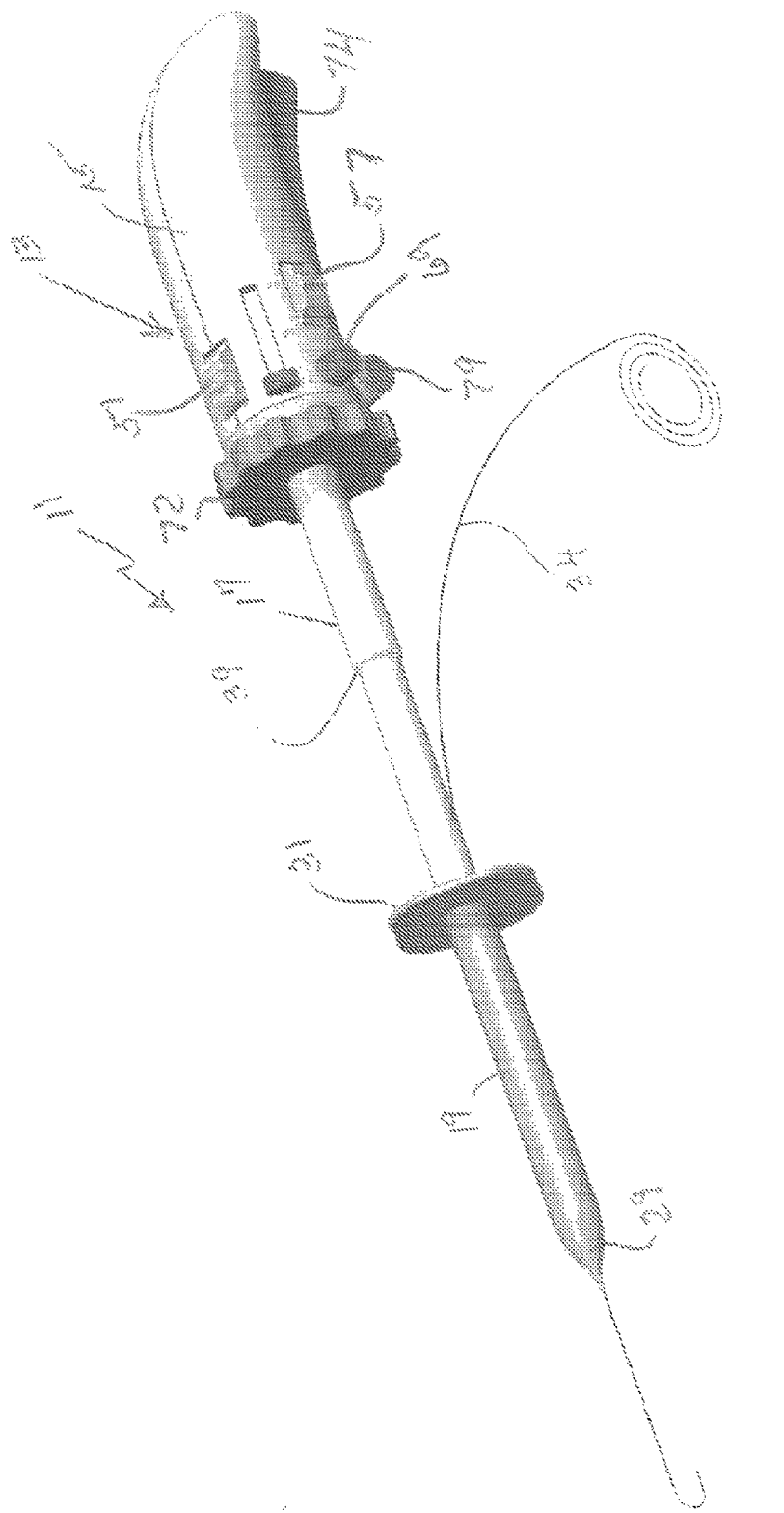

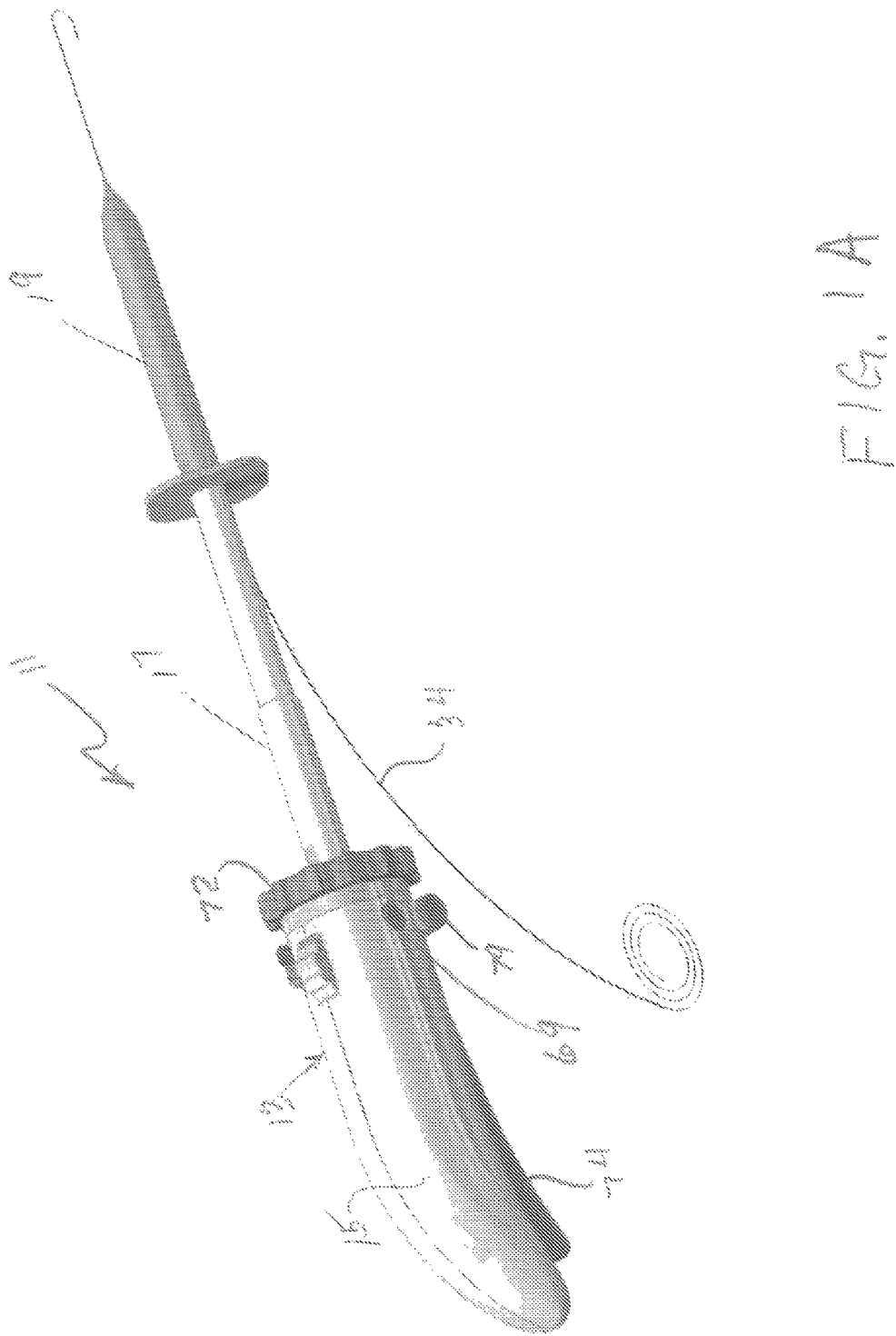

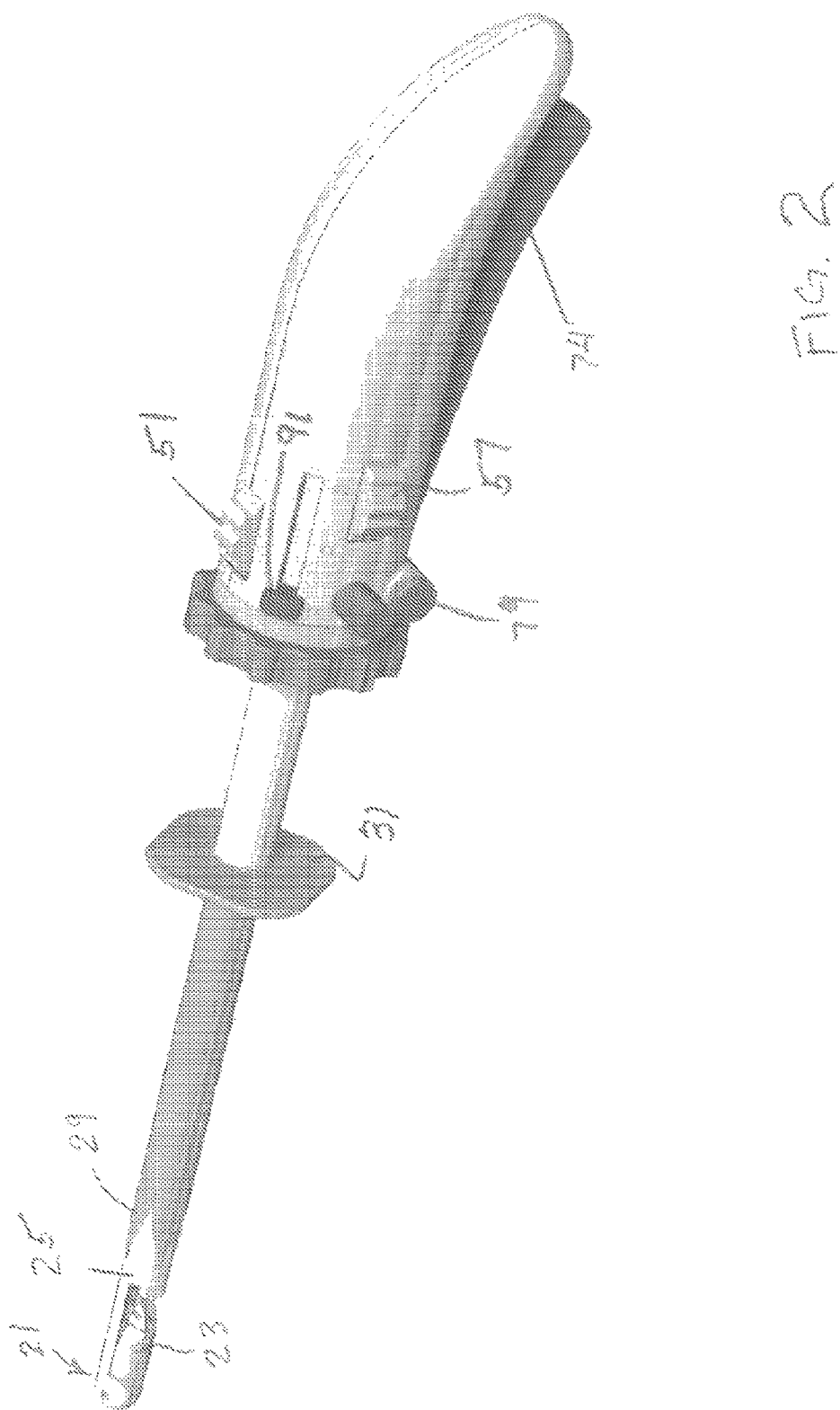

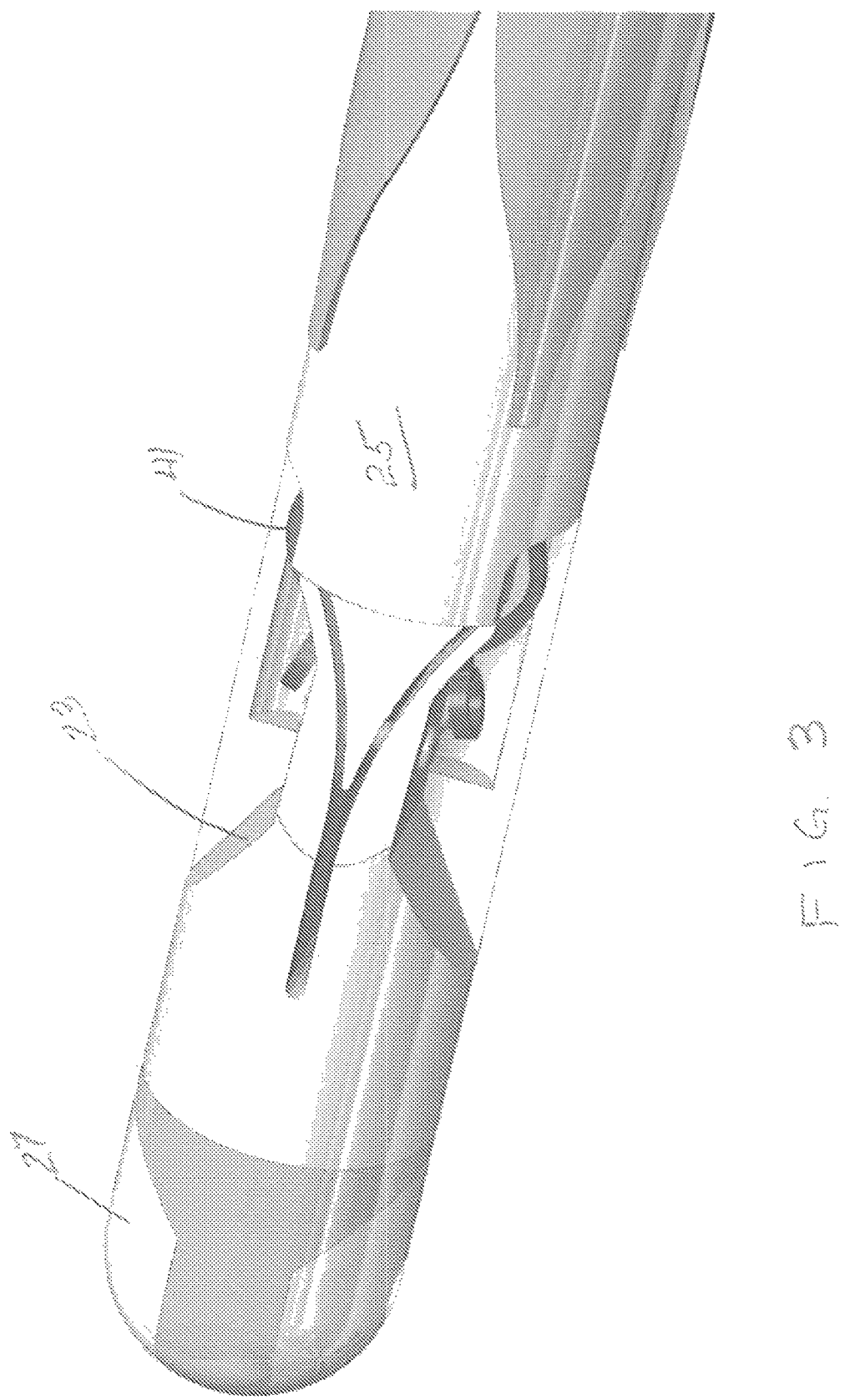

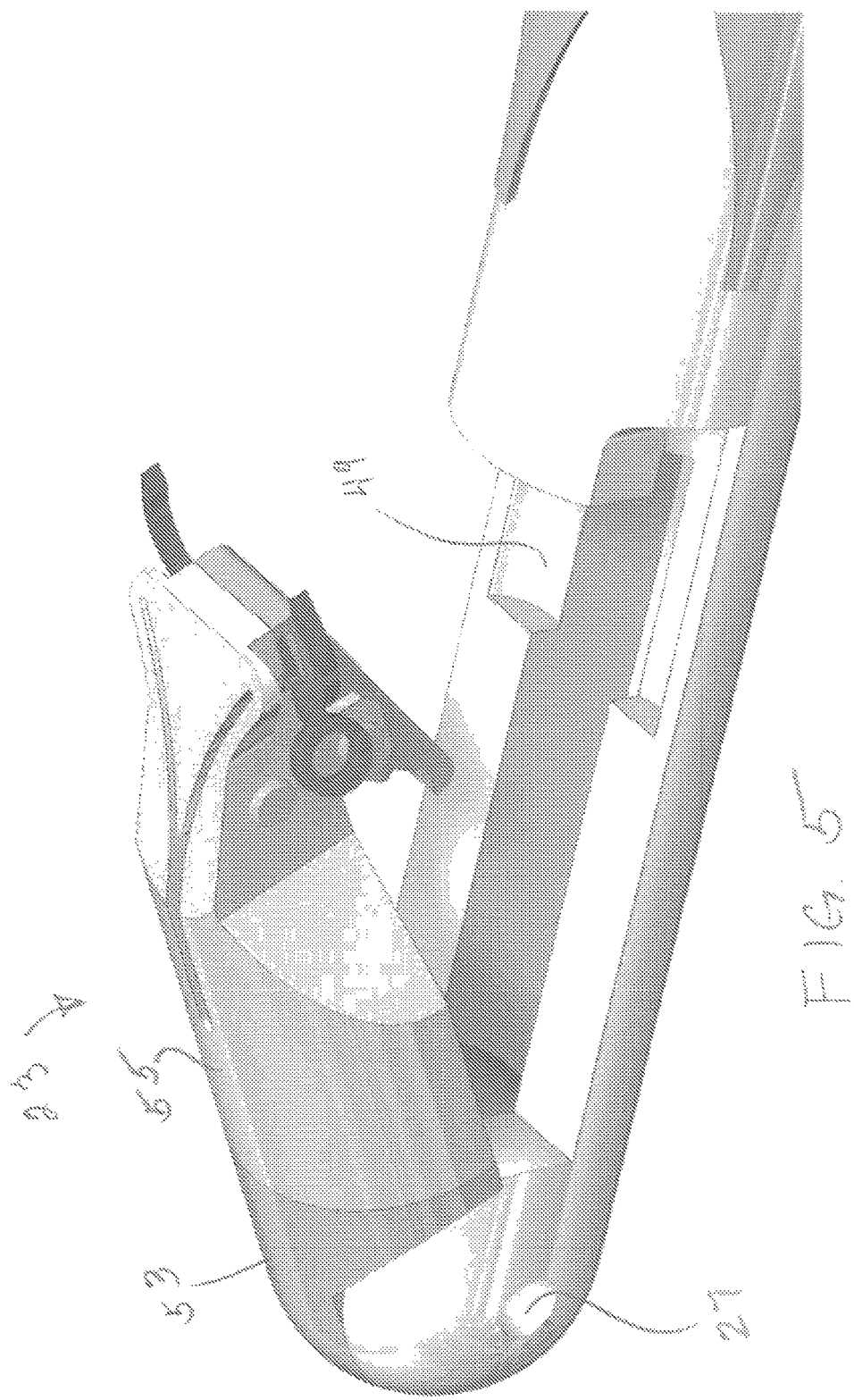

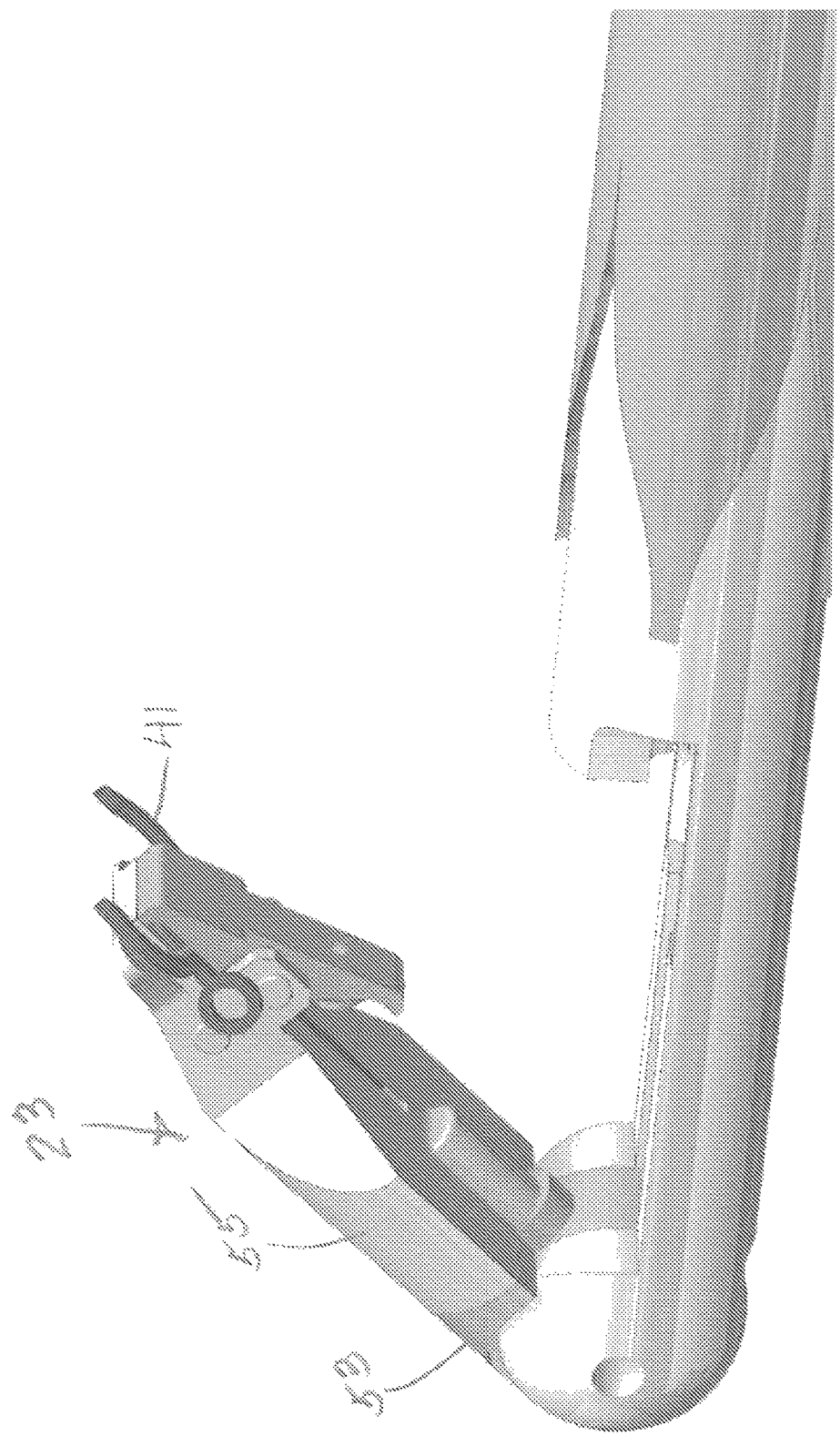

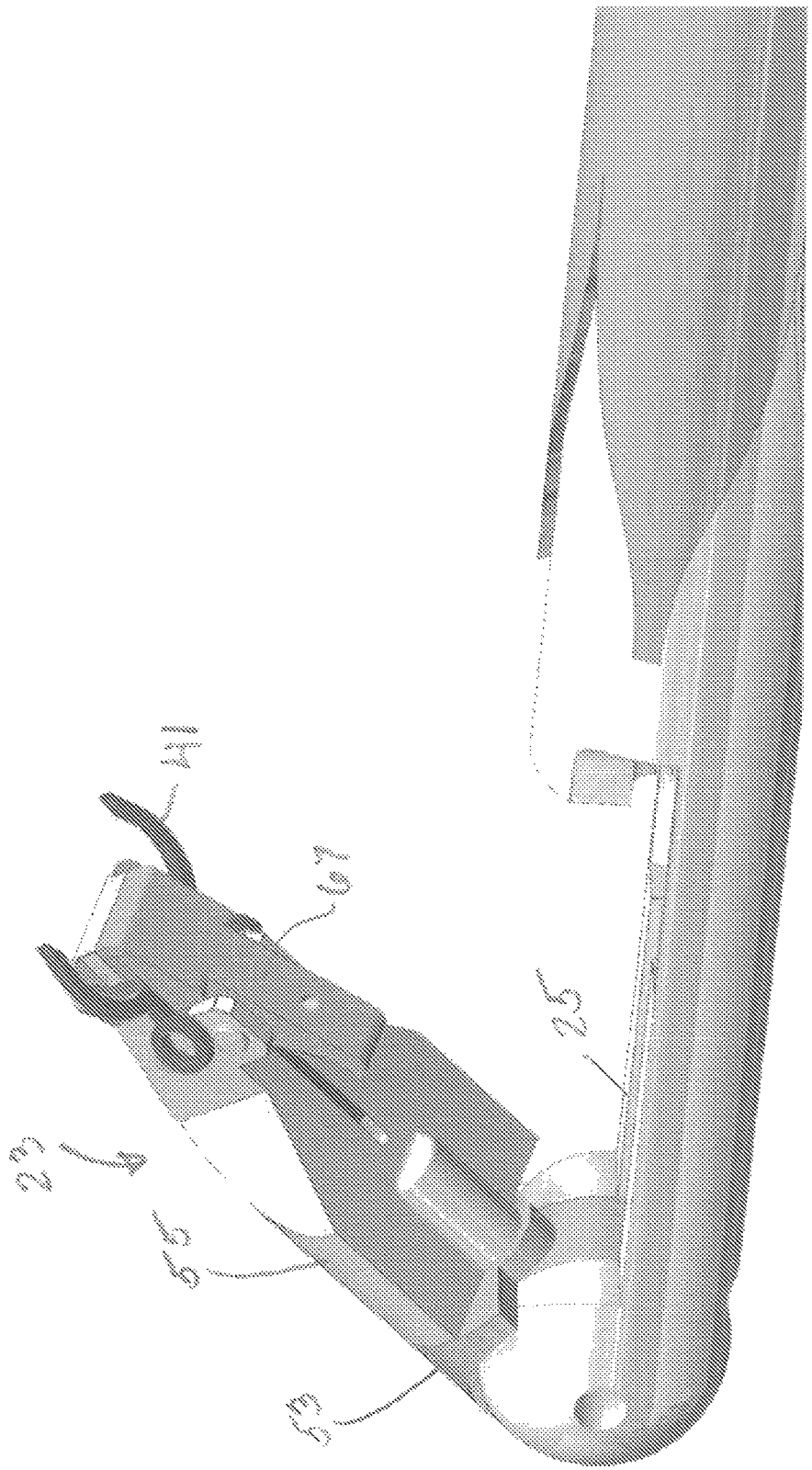

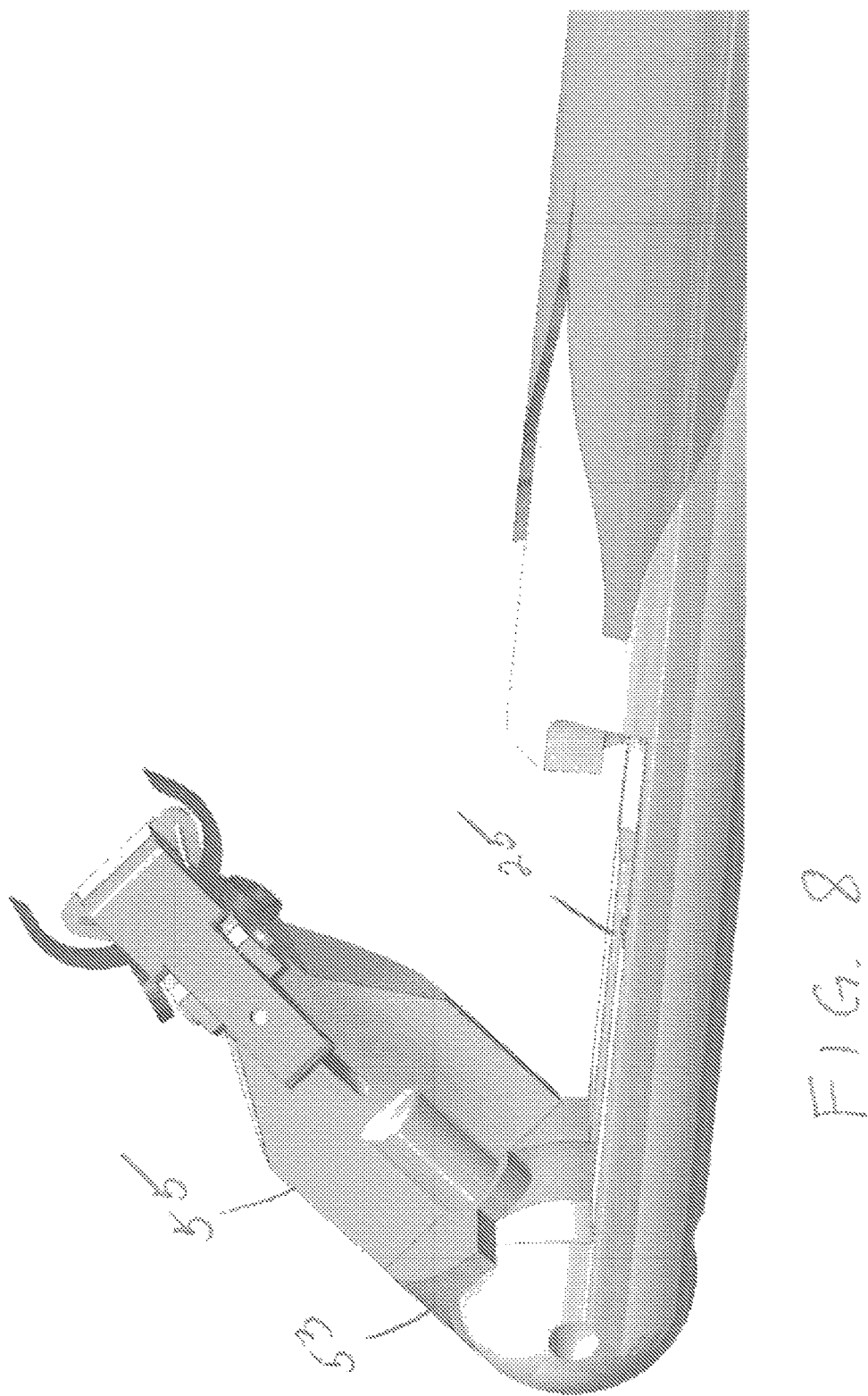

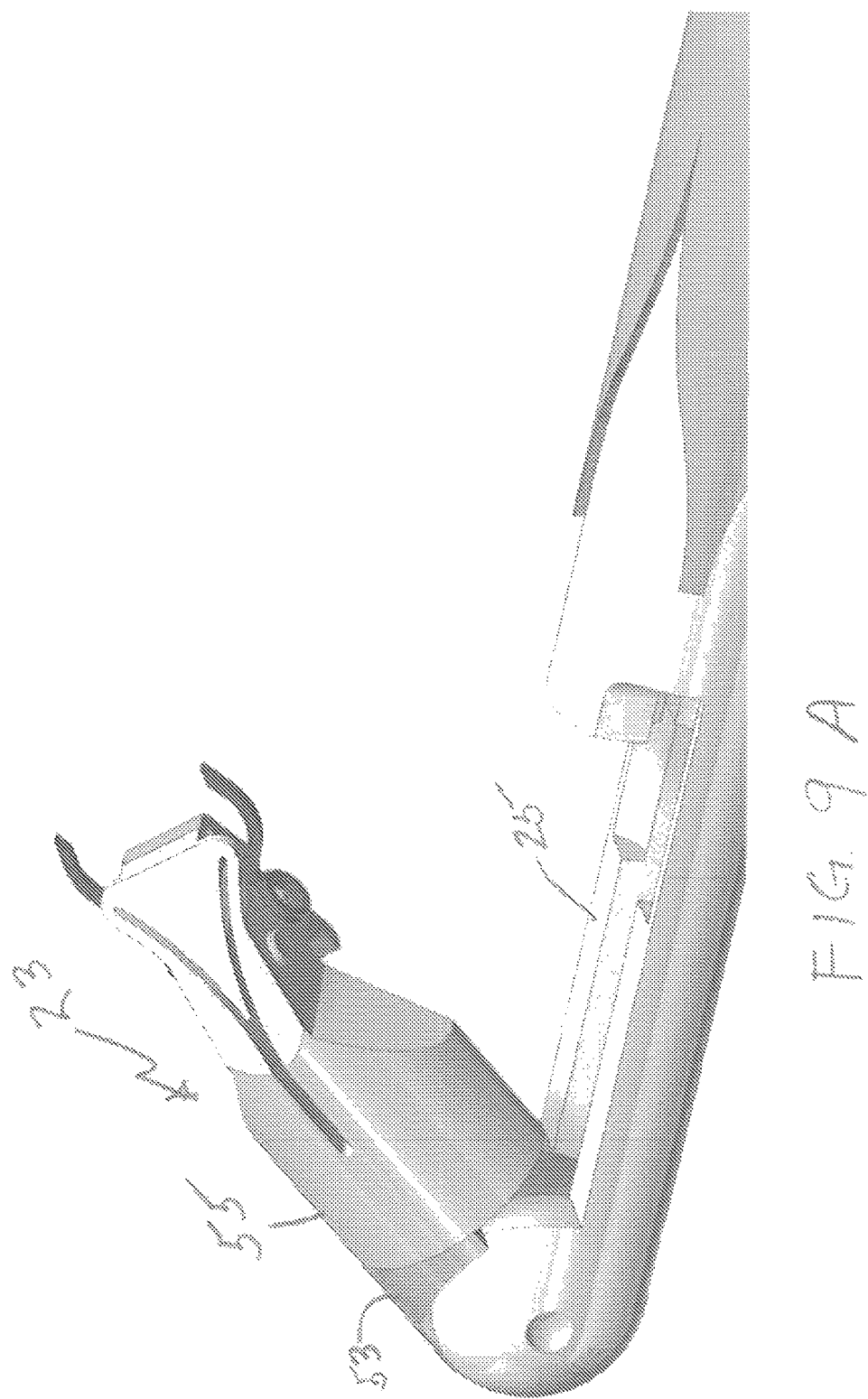

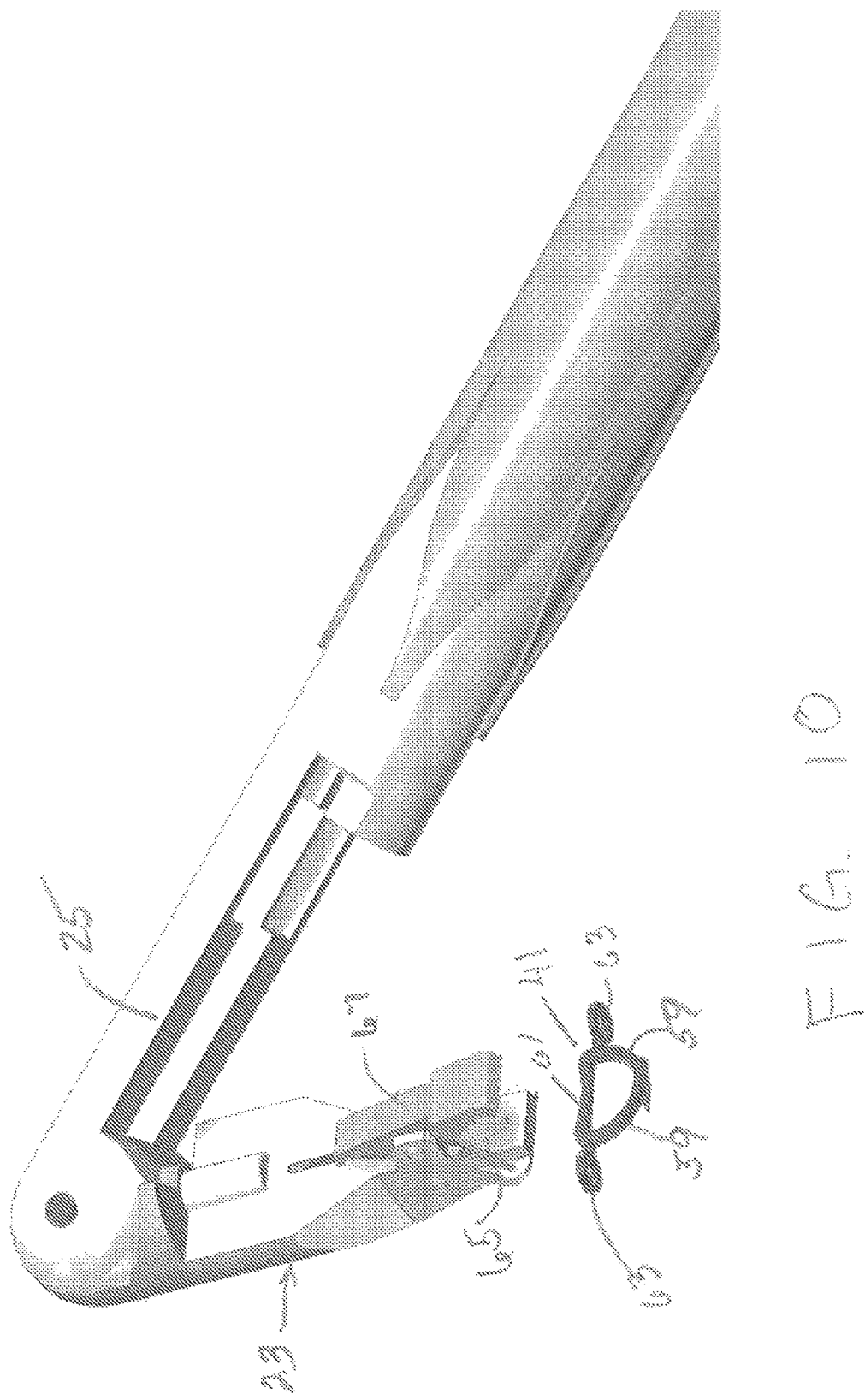

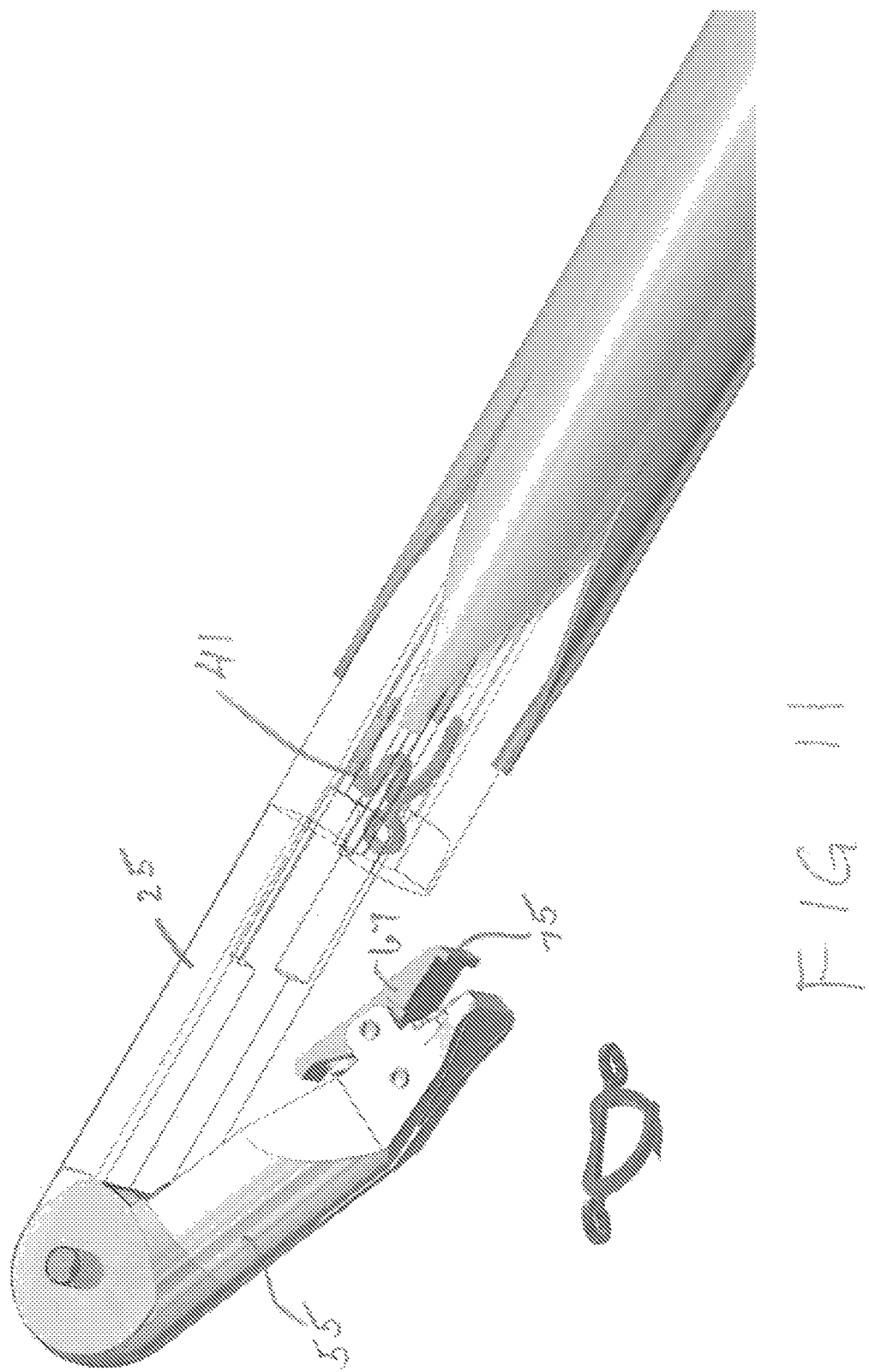

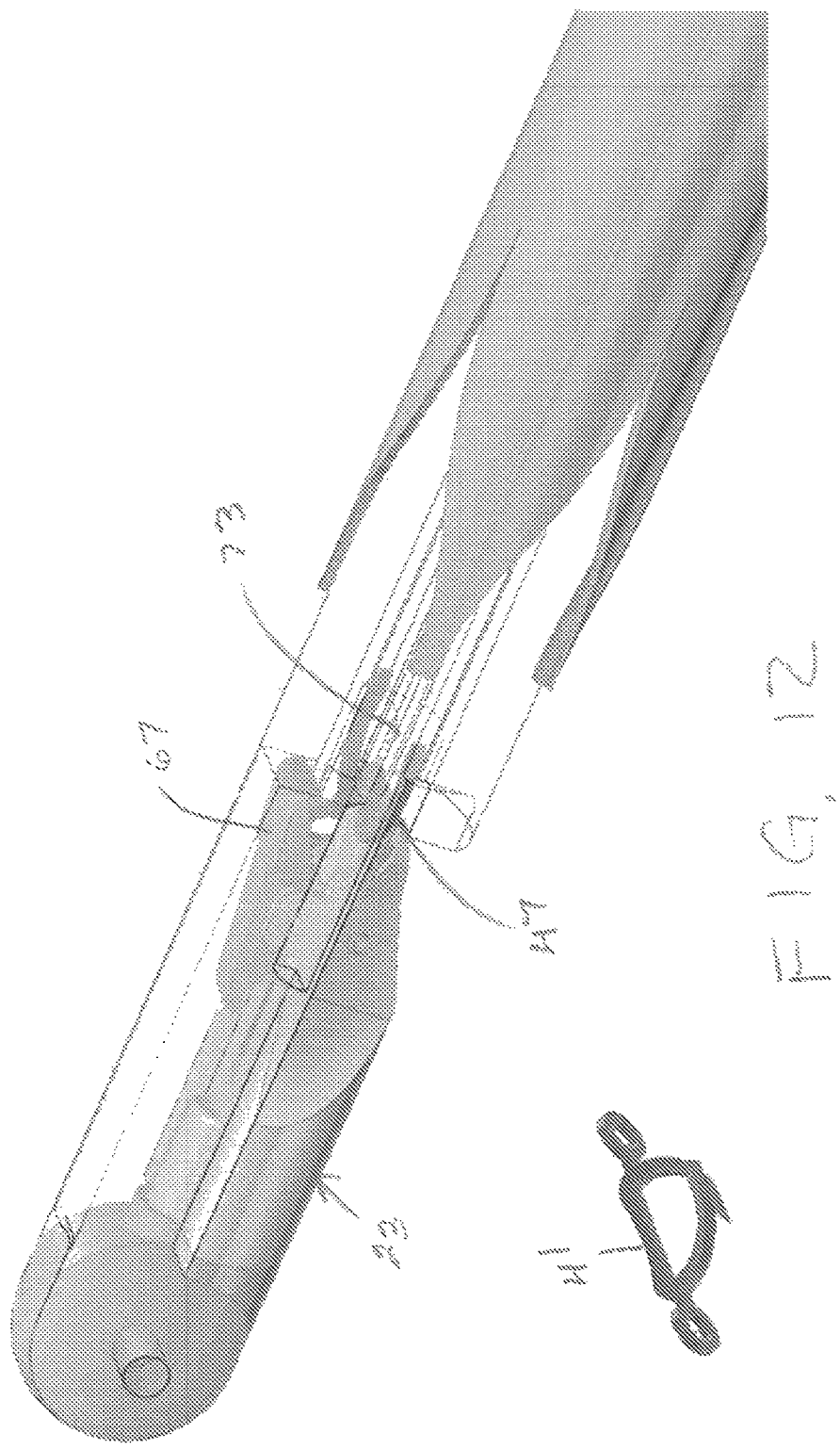

SURGICAL STAPLER

CROSS-REFERENCE TO RELATED APPLICATION

This application is a U.S. national phase application of International Application No. PCT/IB2014/002992, filed Nov. 4, 2014, which claims the benefit of U.S. Appl. No. 61/899,654, filed Nov. 4, 2013, which is are each hereby incorporated by reference in their entirety.

FIELD

This application relates to methods and devices for carrying out surgical stapling within the human body and, in particular, methods and devices for accessing a chamber within the human heart and performing a minimally invasive surgical procedure, such as repairing pathology of a heart valve within a cardiac chamber by stapling while the heart is still beating.

BACKGROUND

Various devices have been developed for carrying out percutaneous minimally invasive surgery within the human body, and various stapling devices have been developed for such procedures. Many of these, such as that shown in U.S. Pat. No. 6,312,447 to Grimes, employ a shape memory staple. Other tools, such as those disclosed in U.S. Pat. No. 8,157,719 to Ainsworth et al., have been proposed for percutaneous minimally invasive heart surgery where a stapling device would be operated within a chamber of a human heart. Although there have been significant advances in this art in the last decade, still further improvements in such devices continue to be sought.

SUMMARY

Advantageously, the stapler can allow for having a hinge and/or rotation connection of a holder of the stapler that is further away from the handle than the holder of the stapler. Further, such a configuration can advantageously allow for insertion of a staple in a direct generally directed away from the hinge and/or rotation connection and toward the handle. The relatively distant hinge allows for force to be applied to the stapler head such that a large part of that force is more or generally parallel but opposite to the forward direction of the handle. In other words, the force pulls the stapler head generally toward the user. This can allow for staples to be applied to tissue such that their prongs are closer to the user than their crown or upper part, which can be advantageous due to the entry point into the heart in the apex, at its bottom, and the staples can be inserted so that their prongs are in the direction of the apex.

The surgical stapler can be made of sufficiently small proportions that it can be effectively delivered to a desired chamber of a patient's heart, either via transapical passage or via entrance through some other opening created in the heart wall. For example, delivery of a stapling device into the left atrium of the heart can be carried out preliminary to effecting annuloplasty of the mitral valve. The surgical stapler is preferably delivered to the desired heart chamber encased within an encompassing sheath along a guide wire that was earlier inserted. Once the desired location is reached, a stapling device is caused to emerge from the sheath within the heart chamber where it can affect the desired procedure, e.g. stapling to constrict tissue of the mitral valve annulus and thus advantageously changing the e shape of the valve to minimize regurgitation and render it again fully operative.

The stapler design comprises a stapling head is hinged to a body at the distal end of an elongated barrel that extends distally from a handle. The head includes mechanism for holding one generally M-shaped surgical staple having two legs terminating in stiff, sharpened prongs that point back at the proximal end of the handle. Preferably, the barrel of the handle contains a magazine of surgical staples which can thereafter be individually loaded into the stapling head.

The illustrated stapler is adapted to implant M-shaped surgical staples of the type generally shown in U.S. Pat. No. 5,725,554 to Simon et al. where the application of force against a pair of shoulders presses the undersurface of the crown connector against an anvil; the fundamentals of this stapler design may be adapted to construct a device that would use shape memory staples. More particularly, the illustrated stapler is adapted to implant staples of the general type shown in U.S. Pat. No. 8,475,491 having a ring connector extending laterally from at least one leg that become interconnected with one another to form a chain.

The stapling head is pivotable away from the longitudinal axis of the barrel of the handle sufficiently to expose the prongs of the staple in a position here they can be caused to penetrate the tissue of the annulus; in an annuloplasty procedure, the prongs will remain in an orientation where they are pointed proximally, i.e. generally back toward the handle. This is because the pivot point of the stapling head is located more distal from the handle than is the stapling head. The surgeon manipulates the stapling device to position the staple at the desired location along the valve annulus, where it is to be implanted in a manner so as to constrict the valve tissue. There is further benefit in using interconnected staples, such as shown in the '491 patent, which not only constrict the annulus, but prevent subsequent remodeling of tissue that can occur if non-interconnecting staples are used because the tissue between staples can elongate over time.

Optionally, the distance between the staple legs can be altered before their penetration into the tissue, e.g. while already loaded into the stapling head, in order to set the desired amount of constriction of tissue that will occur upon implantation of that particular staple. Preferably, the stapling head is reloadable in place within the heart chamber, e.g. by pivoting hack to its initial at rest position, generally aligned with the longitudinal axis of the handle, where a single staple can be grasped from the magazine by a pusher and slid generally along the longitudinal axis and delivered into the stapling head. In addition to the stapling head being pivotable, preferably for at least about 80° from its initial at rest orientation in juxtaposition with the body part at the distal end of the handle, the head, once pivoted, can also be rotated about its axis in either direction, as can the barrel of the stapler itself.

In one particular aspect, a surgical stapler comprises a control handle having a forward-extending barrel having a central axis, a stapling device at the distal end of said barrel, said stapling device comprising a stapling head part, a stapler body part, a hinge connection which pivotally interconnects said two parts, and a generally M-shaped surgical staple having two legs with prongs at the respective ends, said stapling head part comprising mechanism which holds one such surgical staple and implants said staple in tissue by causing said two legs to move toward each other, after puncturing a patient's tissue, to reach a secure final position constricting said tissue, and drive mechanism which pivots said stapling head part to at least about 15° from an at rest position, juxtaposed with said stapler body part, to an active position for implantation of the staple into tissue in a generally proximal direction.

In another particular aspect, the invention provides a surgical stapler which comprises a control handle having a forward-extending barrel having a central axis, a stapling device at the distal end of said barrel, said stapling device comprising a stapler body part, a stapling head part pivotably hinged to said body part, and a surgical staple having two legs with prongs at the respective ends, oriented to point proximally, said stapling head part comprising mechanism which holds one such surgical staple and implants such staple in tissue by causing said two legs to move toward each other, after puncturing a patient's tissue, to a secure final position constricting said tissue, and drive mechanism which can pivot said head part to at least about 15° from an at rest position, juxtaposed with said body part, to an active position for implantation of the staple into tissue in a generally proximal direction.

In a further particular aspect, the invention provides a surgical stapler which comprises a handle having a forward-extending barrel, a stapling device at the distal end of said barrel, said stapling device comprising a stapler body part, and a stapling head part pivotably hinged to said stapler body part, said stapling head part comprising mechanism which holds one surgical staple, having two legs with prongs at respective ends being positioned at a location proximal of the pivot point, and implants such staple in tissue by causing said two legs to move toward each other, after puncturing a patient's tissue, to a secure final position constricting said tissue, a magazine in said barrel containing a plurality of surgical staples, mechanism which can withdraw one of the surgical staples from said magazine and deliver such, with its prongs pointed in the direction of said handle, into said stapling head part at a time when said stapling head part is pivoted into its at rest juxtaposition adjacent said stapler body part, and mechanism which can pivot said stapling head part to at least about 15° from an at rest position juxtaposed with said stapler body part to an active position for implantation of the staple into tissue in a generally proximal direction.

In a still further particular aspect, the invention provides a method of repairing a patient's leaking mitral valve, which method comprises the steps of (a) inserting an endoscopic surgical stapler, having a handle with an elongated body and having a stapling head part, which carries a surgical staple with its prongs oriented in a direction pointing toward the handle disposed, in folded condition with said elongated body, into the left ventricle of a patient's heart through a transapical passageway, (b) moving said stapler through the valve opening between the leaflets of the mitral valve into the left atrium, (c) unfolding said stapler to expose the stapling head part, (d) implanting said staple into the valve annulus adjacent the posterior leaflet with its prongs still oriented in a direction generally toward the handle, whereby the tissue is constricted where the staple is implanted, (e) refolding said stapler and reloading another staple into said stapling head part, (f) unfolding the reloaded stapler and implanting another staple adjacent the implanted staple, (g) repeating steps (e) and (f) to adequately change the shape of the mitral valve annulus so as to effect improved closing of the mitral valve, and (h) refolding said stapler and withdrawing it from the heart of the patient.

BRIEF DESCRIPTION OF THE DRAWINGS

FIG. 1 is a perspective view showing one embodiment of a surgical stapler incorporating various features of the invention, illustrated in connection with a guide-wire, such as is usually first inserted and then used to guide a surgical stapler to an operative location.

FIG. 1A is a perspective view like FIG. 1 shown from the opposite side.

FIG. 2 is a perspective view of the surgical stapler of FIG. 1 without the guide-wire and with the flanged sheath shown in its retracted position.

FIG. 3 is a fragmentary perspective view, enlarged in size, of the distal end of the surgical stapler of FIG. 2 with the barrel rotated slightly clockwise.

FIG. 5 is a perspective view similar to FIG. 4 showing such pivoting to an angle of about 40°.

FIG. 6 is a perspective view similar to FIG. 5 showing such pivoting to an angle of about 65°.

FIG. 7 is a perspective view similar to FIG. 6 showing the end section of the stapling head rotated clockwise about 20°.

FIG. 8 is a view similar to FIG. 7 showing the end section rotated further clockwise to about 60°.

FIG. 9A is a view similar to FIG. 8 with the end section shown rotated counterclockwise about 90°.

FIG. 10 is a view similar to FIG. 9B showing the stapling head withdrawn slightly following implantation and schematically showing the implanted staple.

FIG. 11 is a view similar to FIG. 10 showing the end section rotated back to its zero position and pivoted back part way toward its at rest position, continuing to show the schematic location of the implanted staple while also schematically showing the location in the magazine of the most distal staple.

FIG. 12 is a view similar to FIG. 11 with the stapling head juxtaposed with the body portion and in the process of receiving the staple from the magazine for reloading.

DETAILED DESCRIPTION

Figure 4T:
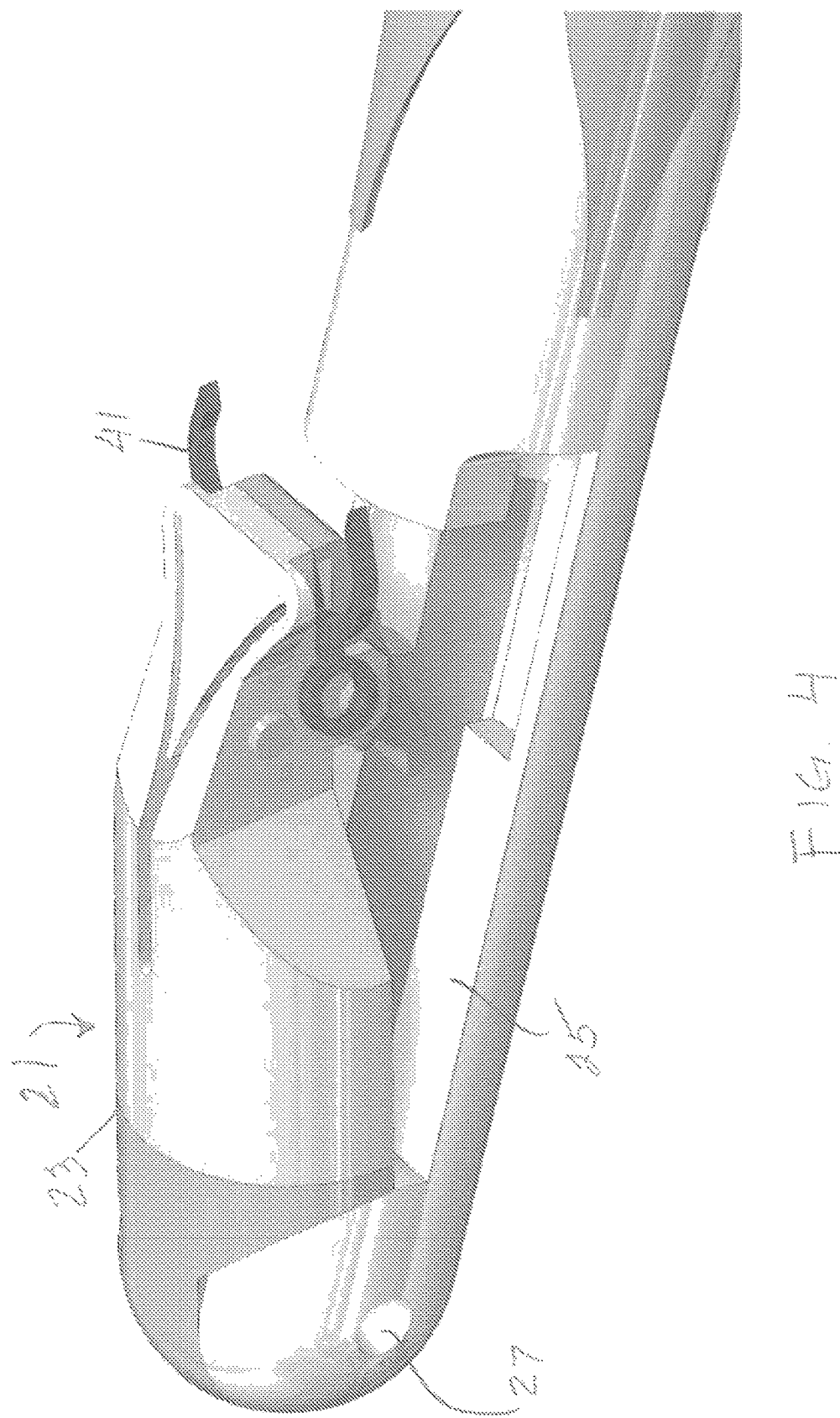
FIG. 4 is a perspective view similar to FIG. 3 with the barrel rotated further clockwise, showing the distal end of the stapler with the stapling head pivoted at an angle of about 20° to the axis of the elongated barrel of the surgical stapler.

Illustrated in FIG. 1 is a surgical stapler 11 which comprises a control handle 13 that is formed with a grip portion 15 at its proximal end and an elongated barrel portion 17 which extends forward therefrom. A flanged sheath or introducer 19 is preferably carried on the barrel portion 17 to envelop and shield it as the surgical instrument is inserted percutaneously into the chest of the patient and into the heart. The surgical stapler 11 is designed for insertion through an incision in the chest of the patient, where it is passed through the apex of the heart, for example, into the left ventricle (LV), and then through the mitral valve into the left atrium (LA). It will be understood that this basic stapling device can be used for other stapling operations within the heart and that it can likewise be developed for other desired particular endoscopic stapling procedures. If adapted for use within a catheter, the sheath may not be employed.

Figure 22:
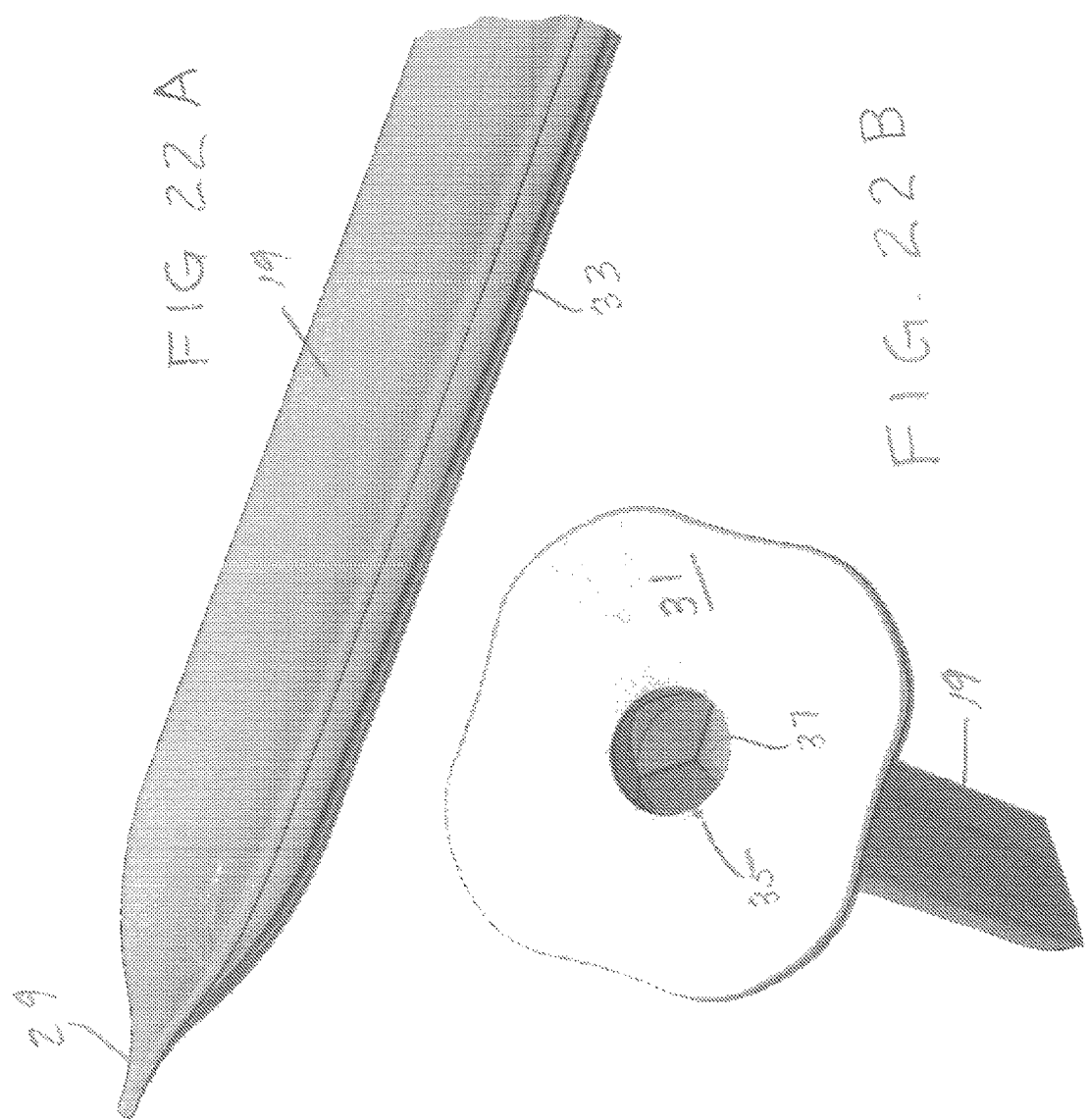
FIG. 22A is a fragmentary perspective of the sheath seen in FIG. 1, showing the tunnel along one lateral edge through which the guide-wire passes.
FIG. 22B is a perspective view looking at the proximal end of the flanged sheath of FIG. 22A showing the small entrance into the tunnel and the interior unidirectional valve near the proximal end of the sheath which would prevent the outflow of blood were the barrel end of the stapler to be withdrawn while the sheath remained in a transapical passageway.

Encased protectively within the sheath 19 is a stapling device 21 at the distal end of the barrel 17 which comprises a stapling head 23 that is pivotably connected to a stapler body 25 by a hinge region or connection 27. When relative movement is effected so that the flanged sheath 19 becomes retracted in a proximal direction, its pointed, split tip 29 is spread apart to cause the emergence of the stapling device 21. A flat flange 31 aligned perpendicular to the longitudinal axis of the sheath is located at its proximal end. The flange 31 allows manipulation of the sheath relative to the elongated barrel 17 of the stapler; however, other devices for manipulating the sheath relative to the barrel of the stapler could alternatively be employed. The sheath 19 is also formed with a tunnel 33 extending along its entire length through which a guide-wire 34 can be conveniently passed, and a small entrance 35 to the tunnel 33 can be seen at the proximal end of the flanged sheath (see FIG. 22B). The sheath also includes an interior unidirectional valve 37 the purpose of which will be explained hereinafter.

From FIG. 1, it can be seen that the elongated barrel 17 of the stapler is stepped at the location 39, and the sheath 19 is slidably received on the lesser diameter, distal portion of the barrel. Thus, the sheath 19 can be withdrawn no further proximally than the orientation shown in FIG. 2 where it abuts the step 39; at this relative location, the stapling mechanism has been exposed to its operative position. Moreover, the length of the sheath 19 and the barrel are used as a safety feature so as to prevent the insertion of the distal end of the stapler too far through the mitral valve where it might cause injury at the upper end of the LA; for example, the length of the sheath might be sized such that the flange 31 might abut the skin of the patient and thereby limit the insertion of the distal tip of the stapler. Although a stapler might be designed to interconnect a guide-wire with the barrel and exclude a sheath, a protective sheath or introducer is preferred.

Figure 23:
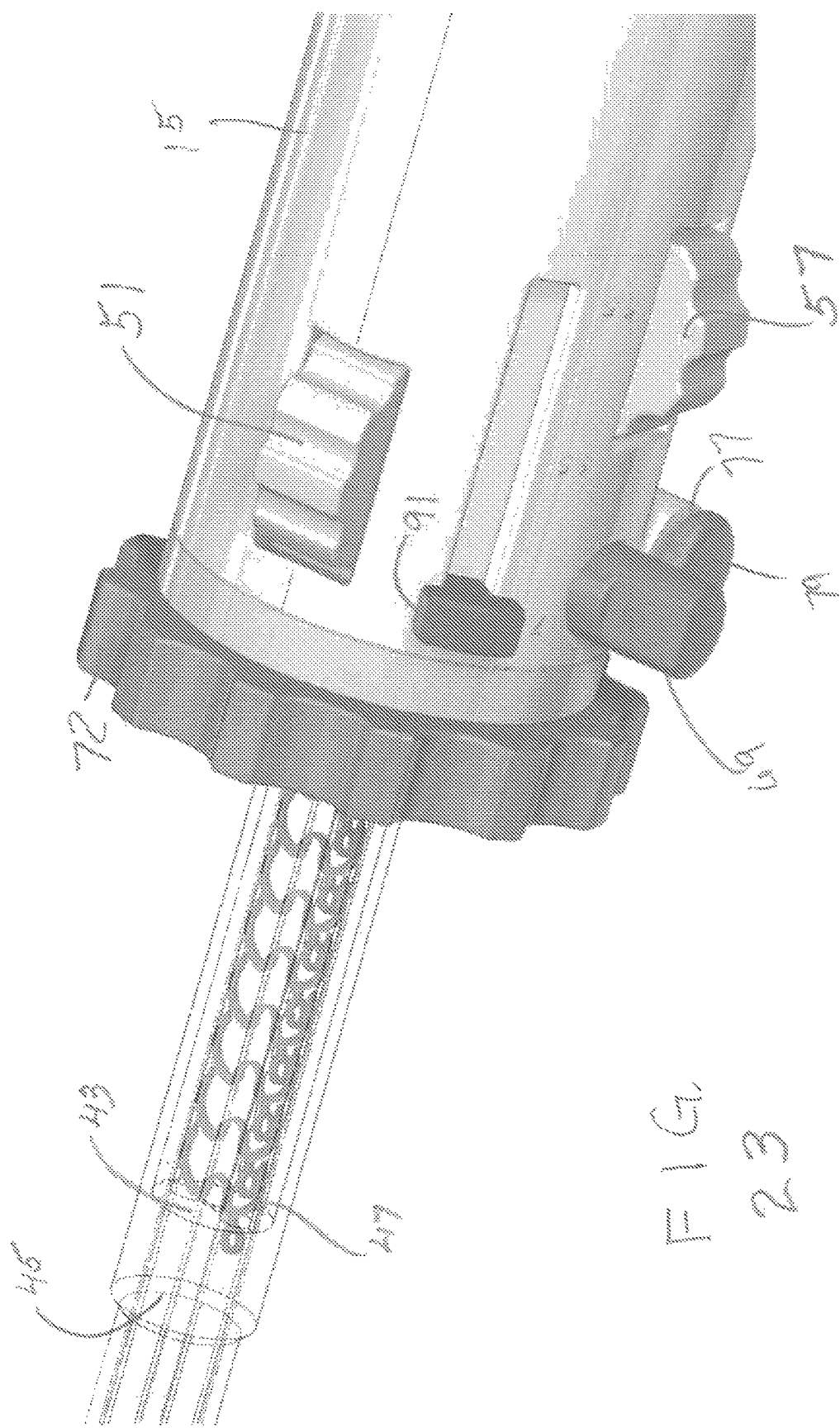
FIG. 23 is an enlarged fragmentary perspective view of the stapler of FIG. 1 showing the barrel schematically.

The stapling head 23 is designed to hold and implant a single staple 41. After such implantation has been accomplished, the head 23 is returned to an "at rest" position in juxtaposition with the body 25 where it is preferably reloaded with a staple 47 from a magazine 43 of staples contained within a hollow region 45 within the elongated barrel 17 located proximal of the body part 25 that is constructed at the distal end. The magazine 43 contains a series of staples 47 within a cartridge of cylindrical exterior surface that resides in the cylindrical hollow region 45 provided in the elongated barrel 17 of the stapler, as best seen in FIG. 23. The illustrated staples 47 which are loaded into the magazine are of a design similar to the staple 41 but have a ring extending laterally from only one leg of the staple, the reason for which being explained hereinafter. The generally M-shaped staples 47 are formed with an essentially planar or flat body that comprises a pair of rigid legs each of which ends in a sharpened prong and a crown connecter. In its initial configuration, the crown connector has the general shape of a U; its U-shape is flattened to a substantially straight configuration upon implantation. In the illustration shown in FIG. 23, the ring of the staple 47 is shown affixed to the left hand leg of each of the staples in the magazine, the bodies of which lie in a common plane aligned to include the centerline of the barrel, with the ring being perpendicular to that plane. The very first staple 41 that is initially implanted has two symmetrical O-rings, as well seen in FIGS. 3-10. This first staple 41 may be mounted in the stapling head 23 by the manufacturer; the remaining staples 47 from the magazine 43 will all have one O-ring only. This first staple having two symmetrical O-rings is preferably deployed first at the middle of the annulus of the posterior mitral leaflet. The following staples can be deployed alternatively on each side, one at a time, allowing thus symmetrical shortening of the annulus of the posterior leaflet.

FIGS. 1 and 1A show a surgical stapler 11 embodying various features of the present invention from both sides. The stapler 11 is illustrated with the flanged sheath 19 at its distal end and with a guide-wire 34 extending through the tunnel 33 along the side of the sheath and protruding from its distal end. FIG. 2 shows the surgical stapler 11 without the guide-wire and with its distal end protruding from the split end 29 of the sheath as a result of relative movement between the sheath 19 and the elongated barrel 17 of the stapler. Such movement is facilitated by the flat flange 31 at the proximal end of the sheath, and it may be accomplished by manual withdrawal, or by pressing the flange against the flesh of the patient's chest adjacent the percutaneous entry slit through which the distal end 29 of the sheath is inserted. Insertion of the surgical stapler 11 will usually follow along a guide-wire 34 that was previously put in place, as explained in more detail hereinafter.

In FIG. 2, the sheath 19 is shown as having been retracted to the step 39 in the elongated barrel portion 17 of the handle so it exposes the stapling device 21 at the distal end of the barrel. The stapling device 21 comprises the stapling head part 23 that is connected to the stapler body part 25 at the end of the barrel by a hinge connection 27 so that it can be pivoted outward from its at rest position shown in FIG. 2 where it juxtaposes with the stapler body part. FIG. 3 is an enlarged fragmentary perspective of the distal end of the surgical stapler, taken from a different angle than that in FIG. 2, which shows a staple 41 that is held in the stapling head 23 with its prongs at the end of its two legs pointed proximally back at the grip portion 15 of the handle.

FIG. 4 shows the stapling head 23 having pivoted about 15° from its juxtaposed position with the stapler body part 25, exposing the stapling head and the prongs at the ends of the staple 41. FIG. 5 shows the pivoting further to an angle of about 30° to the longitudinal centerline of the barrel, and it illustrates a cavity 49 within the stapler body part 25 where the staple 41 and a portion of the stapling head are received in the at rest position. The pivoting movement of the stapling head 23 is effected by the control handle by rotation of a knurled wheel 51 on the grip portion 15 of the control handle. This knurled wheel 51 at the upper ridge of the grip portion 15 of the control handle connects via mechanism that traverses the length of the elongated barrel 17 to cause the pivoting of the stapling head 23.

In FIG. 6, the stapling head 23 is shown as having pivoted to about 60° from its at rest position juxtaposed with the body part. It is believed that the stapler should be designed to pivot the stapling head 23 at least about 60°, and preferably at least about 80° to facilitate the desired annuloplasty procedure for which it has been designed. However, the stapler might also be designed so as to pivot the stapling head up to 180°, i.e. so that it extends straight distally from the barrel, if desired for some particular endoscopic stapling procedure. Generally, the operation of the surgical stapler 11 will be such that pivoting of the stapling head 23 for at least about 15° and preferably for at least about 25° will be effected so as to space the staple sufficiently offset from the elongated barrel to allow the staple to be implanted in a generally proximal direction without interference from the presence of the adjacent barrel.

Figure 9B:
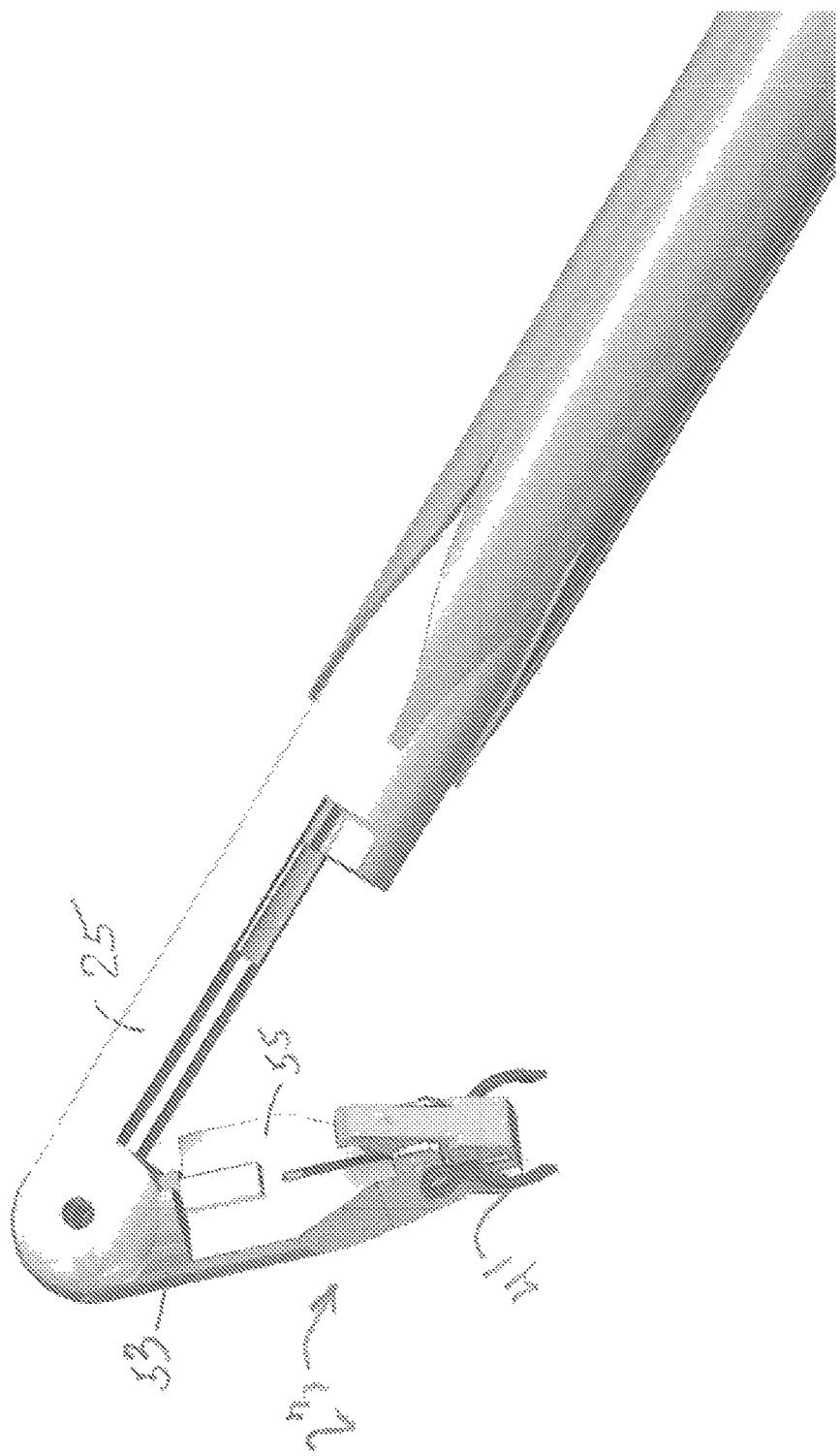
FIG. 9B is a perspective view of the distal end of the stapler as seen in FIG. 9A shown inverted and taken looking at the opposite surface.

The stapling head 23 is formed with a base section 53 and a rotatable end section 55, as can be seen in FIG. 7 where the end section has been rotated about 20° clockwise from its initial zero position in the at rest orientation of the stapling head. The rotation of the end section 55, which carries the staple 41, relative to the base section 53 is controlled by another knurled wheel 57 located on the left hand side of the grip portion 15 of the control handle, which likewise contains linkage extending through the barrel 17 to the hinge region 27 at the distal end of the surgical stapler. FIG. 8 shows further rotation clockwise to about 60° from the zero position. Rotation can be in either direction, clockwise or counter-clockwise, from the zero position, and FIG. 9A shows rotation of the end section 55 of the stapling head 23 about 90° in the counter-clockwise direction from the zero position, FIG. 9B illustrates the distal end of the stapler with an inverted orientation to that in FIG. 9A, and it is noted that the staple 41 in the rigid stapling head 23 remains oriented with its prongs pointing proximally, i.e. in the general direction back toward the grip portion 15 of the control handle. With this orientation of the rigid head 23 when stapling into the tissue, force can controllably be applied to the staple so that its prongs are pushed against the tissue with precise force. With the stapling head 23 being generally pointed toward the handle, the surgeon can carefully pull back on the control handle 13 with steady exact motion when the stapling head is adjacent the tissue and at a sharp (but inverted) angle to the barrel centerline. As a result, the desired force vector is readily created, essentially pulling the rigid stapling head 23 and the loaded staple towards the tissue with the staple oriented transverse, and preferably generally perpendicular, to the tissue surface.

FIG. 10 illustrates the distal end of the surgical stapler after the staple 41 has been implanted into the tissue and the stapling head 23 has been slightly withdrawn. The implanted staple 41 is shown schematically with its central crown connector 61 now straightened and with its legs 59 crimped so that the prongs lie adjacent each other. The staple 41 has two rings 63 extending laterally respectively from the two legs 59 which are employed to form an interconnected chain of staples that effects the desired annuloplasty as disclosed in the '491 patent. The stapling head 23 in FIG. 10 is shown in its open position exposing its holder region 65 wherein an M-shaped staple is received and held within the holder by a pivoting clamp 67. The clamp 67 is shown in its release position to which it is moved following the implantation of the staple.

In FIG. 11, the stapler is illustrated where the stapling head end portion 55 has been rotated back to its zero position and where the head 23 has been pivoted toward the body part 25 as it is returning to its at rest, juxtaposed location. The clamp 67 remains in its release or open position during return to the at rest position.

As best seen in FIG. 23, the hollow barrel 17 includes a plurality of staples 47 disposed in a cylindrical holder or magazine 43 and aligned so that each staple lies with its body in a common plane that preferably includes the central axis of the barrel. The staples 47 in the magazine have only a single ring disposed laterally from one leg. In FIG. 23, the magazine is oriented so that the ring is attached to the leg at the left hand side of the staple within the barrel. For convenience of the surgeon, the stapler 11 is designed so that the magazine 43 can be rotated 180° so that the ring-carrying leg of the staple is at the right hand edge of the staple in the barrel of the stapler. Rotation of the magazine for 180° is effected by a slide 69 near the distal end of the grip portion 15 of the control handle. The slide 69 can be moved transversely across the diameter of the grip portion 15 and is arranged so that when the end of the slide 69 protrudes from the left hand side of the grip portion, the staples are so orientated as seen in FIG. 23 with the ring-carrying leg to the left. When the slide is pressed inward to the right so that it protrudes from the right hand surface of the grip portion, the magazine has been rotated 180° so that the ring is now attached to the leg on the right. This can result in omitting the need of rotating the entire, fixed delivery device in 180° in order to enable symmetrical deployment on alternative sides of the initial, double O-ring, first staple.

FIG. 11 schematically illustrates the most distal staple 41 in the magazine with its ring carrying leg oriented on the left hand side of the staple. The illustrated staple is a M-shaped staple wherein the crown connector is formed in an essentially U-shape, in which shape it initially exists until it is implanted by action thereupon by a former mechanism as explained hereinafter.

FIG. 12 schematically shows the stapling device 21 having been returned to its at rest position. In FIG. 12, the barrel has been rotated 180° from the orientation of FIG. 1. Rotation of the entire barrel 17 relative to the grip portion 15 for 360° is accomplished by turning the transversely oriented knurled wheel 72 at the distal end of the grip portion. In this orientation, the ring-carrying leg is on the right hand side relative to the grip portion 15. The staple 47 is shown in the process of being delivered into the holder region 65 of the stapling head 23 by an extraction and loading mechanism 73 that includes a pusher which engages a proximal facing surface of the staple. In this position, the clamp 67 remains in the open position so as to receive the staple 47.

Figure 13:
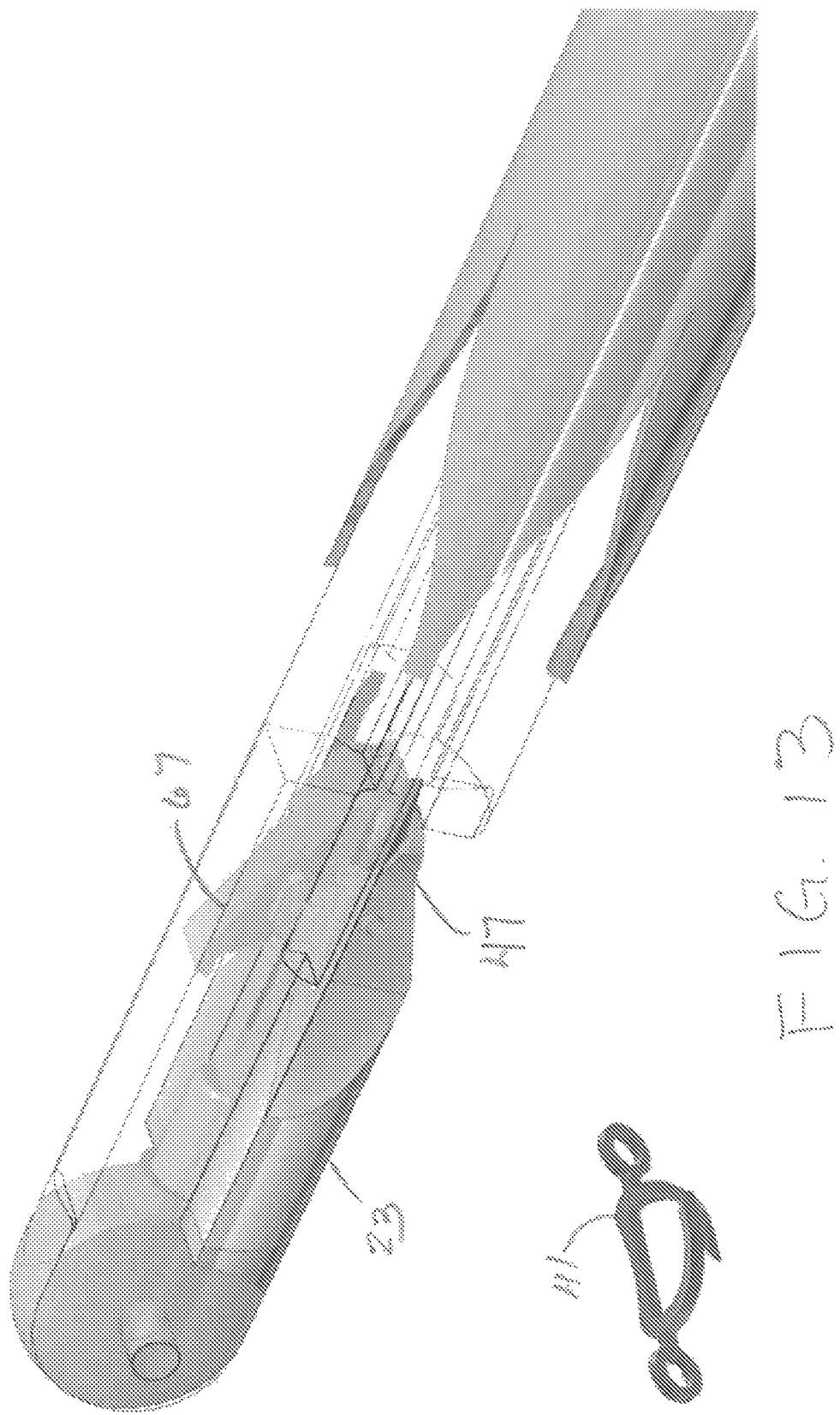
FIG. 13 is a view similar to FIG. 12 showing the reloaded stapling head.

In FIG. 13, the delivery of the staple 47 has been completed, and the extraction and loading mechanism 73, which is operated by a lever 74 located in a slot in the undersurface of the grip portion 15, has closed the spring-loaded clamp 67 and loaded the spring-loaded former mechanism 71 so that it is cocked and ready to implant the staple 47. The clamp 67 includes an anvil section 75 at its end which is moved into abutment with the facing surface of the holder region 65 in the loaded condition so that it lies adjacent the undersurface of the U-shaped crown connector of the staple 47.

Figure 14:
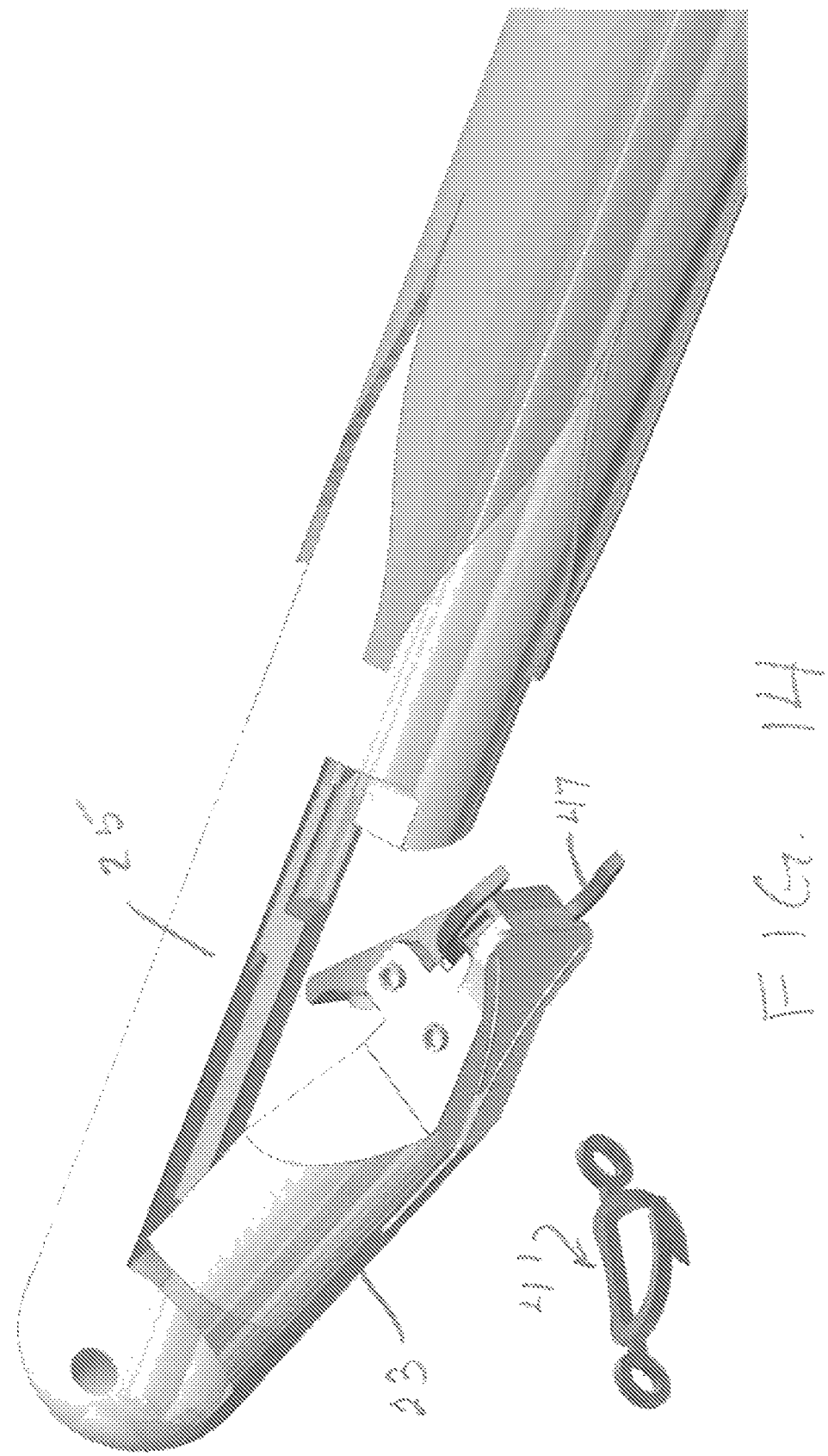
FIG. 14 is a view similar to FIG. 5 showing the stapling head carrying the reloaded staple after having pivoted from the at rest position.
Figure 15:
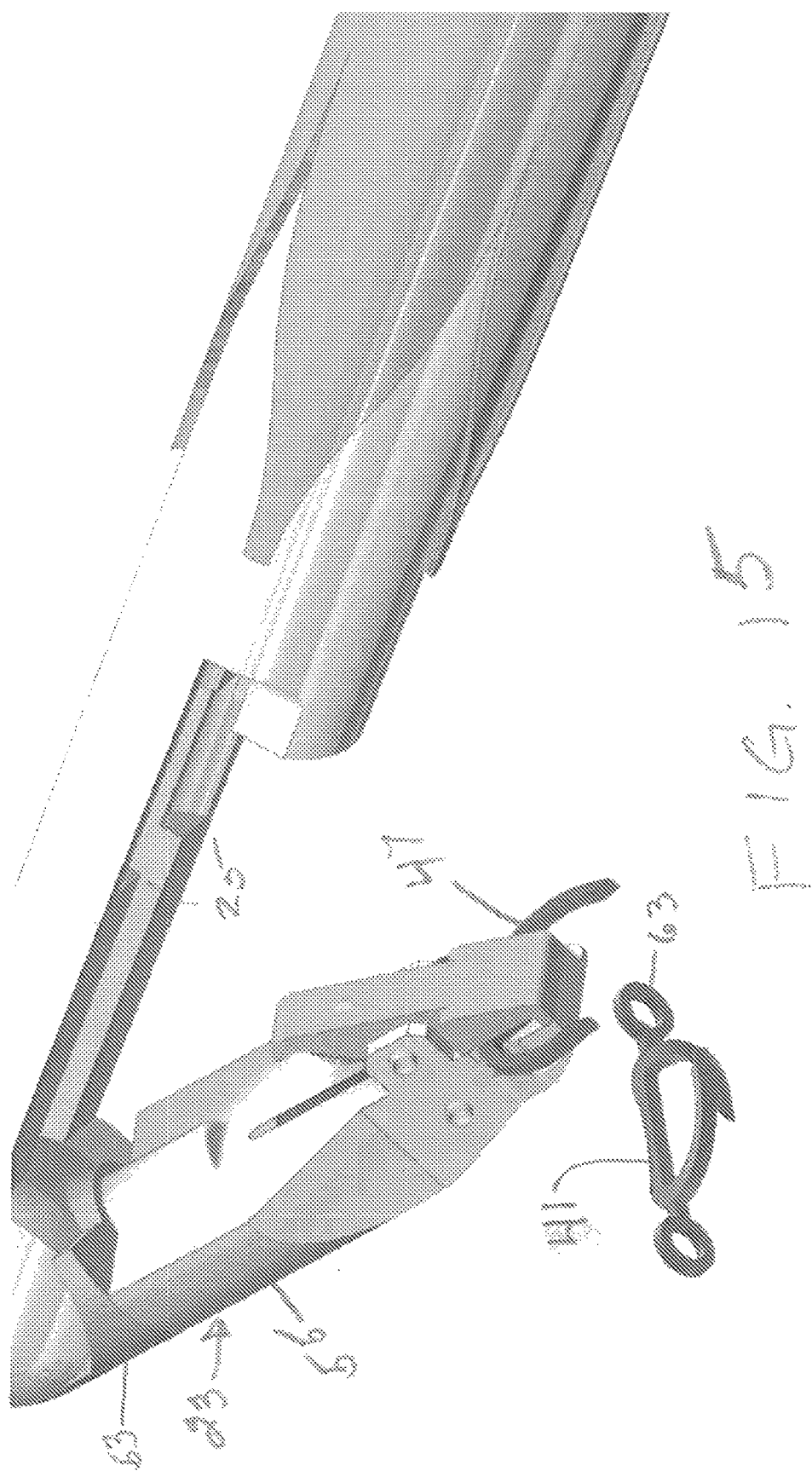
FIG. 15 is a view of the distal end of the stapler shown in FIG. 14 with the end section rotated and the stapling head pivoted to align one prong of the staple that it carries with the ring on the right hand side of the implanted staple.
Figure 16:
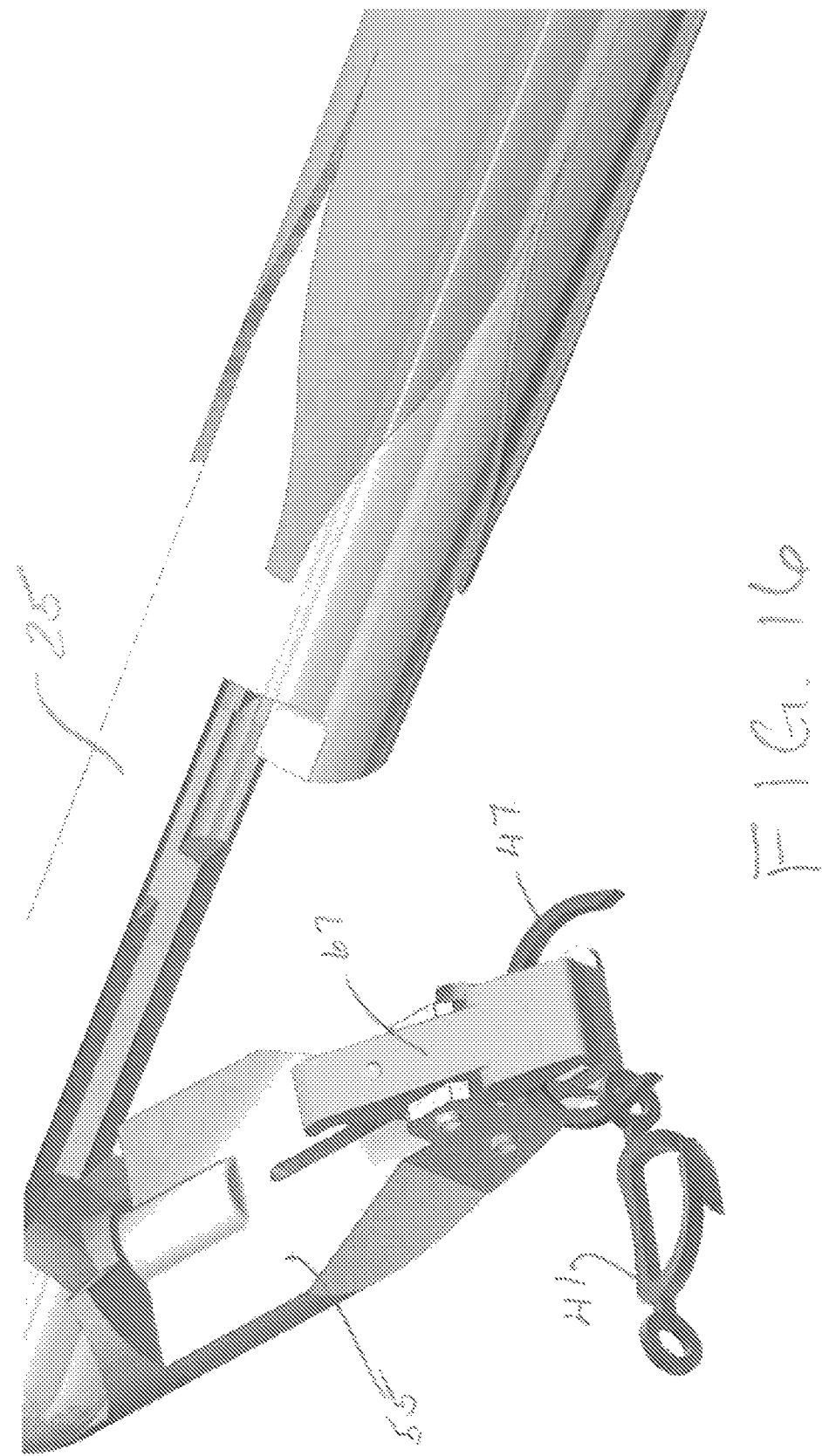
FIG. 16 is a view similar to FIG. 15 showing the position where there would be initial penetration of the prongs of the staple into the heart valve tissue with one prong having passed through the ring.

FIG. 14 shows the stapling head 23 (with the staple 47 loaded) pivoted away from the body part 25 to expose the prongs of the staple which are pointed proximally relative to the grip portion 15. FIG. 15 shows further pivoting of the stapling head 23 and rotation of the end section 55 relative to the base 53 to align the staple 47 so that its leg which does not carry the ring is aligned with the center of the ring 63 on the right hand side of the implanted staple 41. FIG. 16 shows subsequent movement by the surgeon of the surgical stapler 11 so that the leg of the staple 47 passes through the ring 63 and now penetrates the heart valve tissue of the patient.

Figure 17:
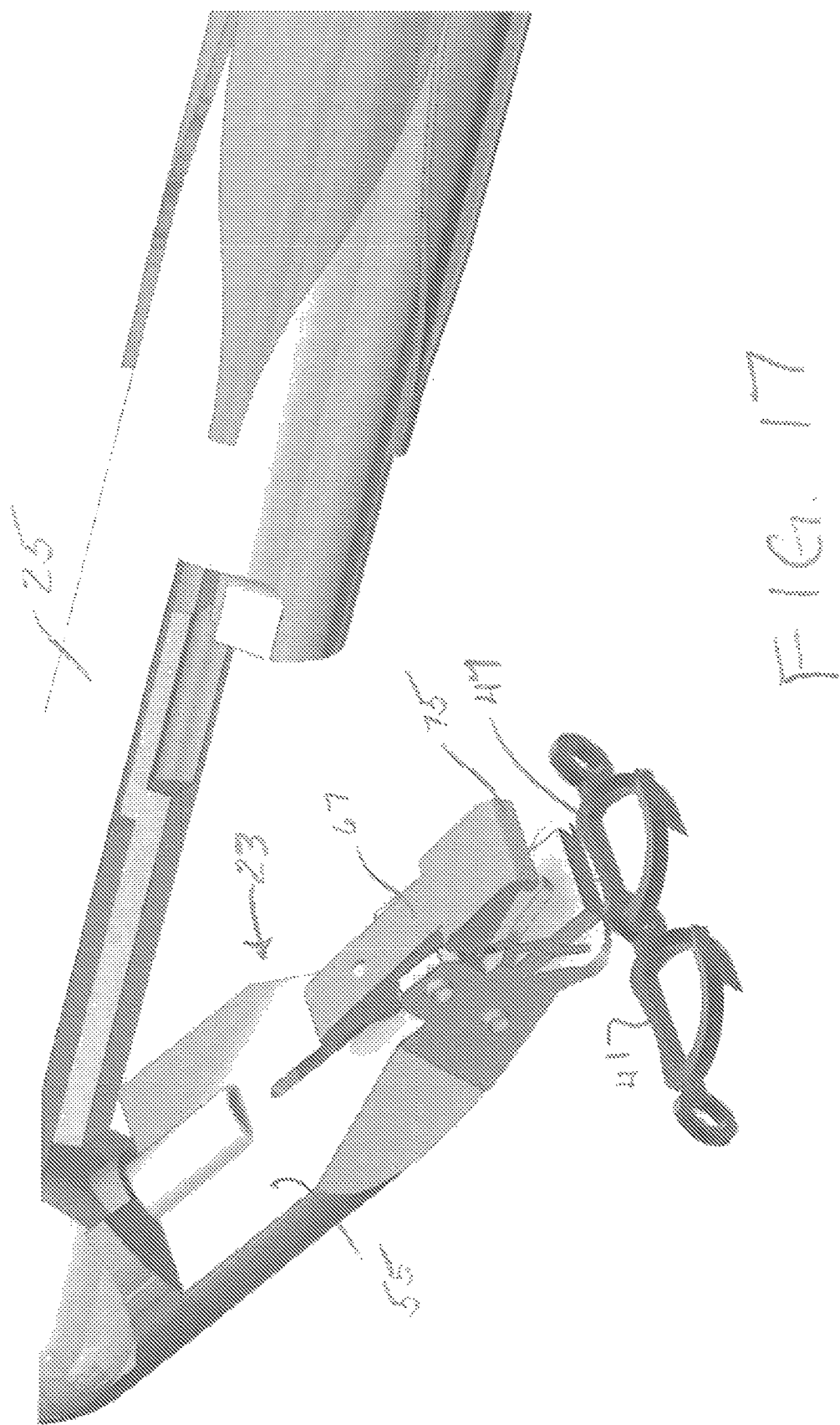
FIG. 17 is a view similar to FIG. 10 schematically showing the two implanted staples and the stapling head withdrawn slightly.

Sensors are located in the stapling head 23 so as to determine that both prongs of the staple 47 are symmetrically penetrating into the heart valve tissue as indicated by having surpassed a minimal determined pressure threshold. Such sensors may be mechanical or electronic and are designed to send a signal to a trigger mechanism 77. The trigger mechanism 77 includes a pair of triggers 79 disposed substantially coaxially on opposite sides of the grip portion 15 of the handle, and simultaneous pressing of the two oppositely disposed triggers 79 is required to actuate the trigger mechanism 77. This spatial disposition of a pair of coaxial triggers 79 positively guards against the surgeon inadvertently slightly moving the control handle at the movement of implantation. The trigger mechanism 77 actuates the spring-loaded former mechanism 71 which presses the upper surfaces of the shoulders of the M-shaped staple 47 forward, causing the U-shaped crown connector with its undersurface resting on the anvil 75 to be reshaped into a straight connector, as the two legs move past one another to the orientation shown in FIG. 17 where the staple 47 has become interconnected with the staple 41 that was first implanted.

Figure 18:
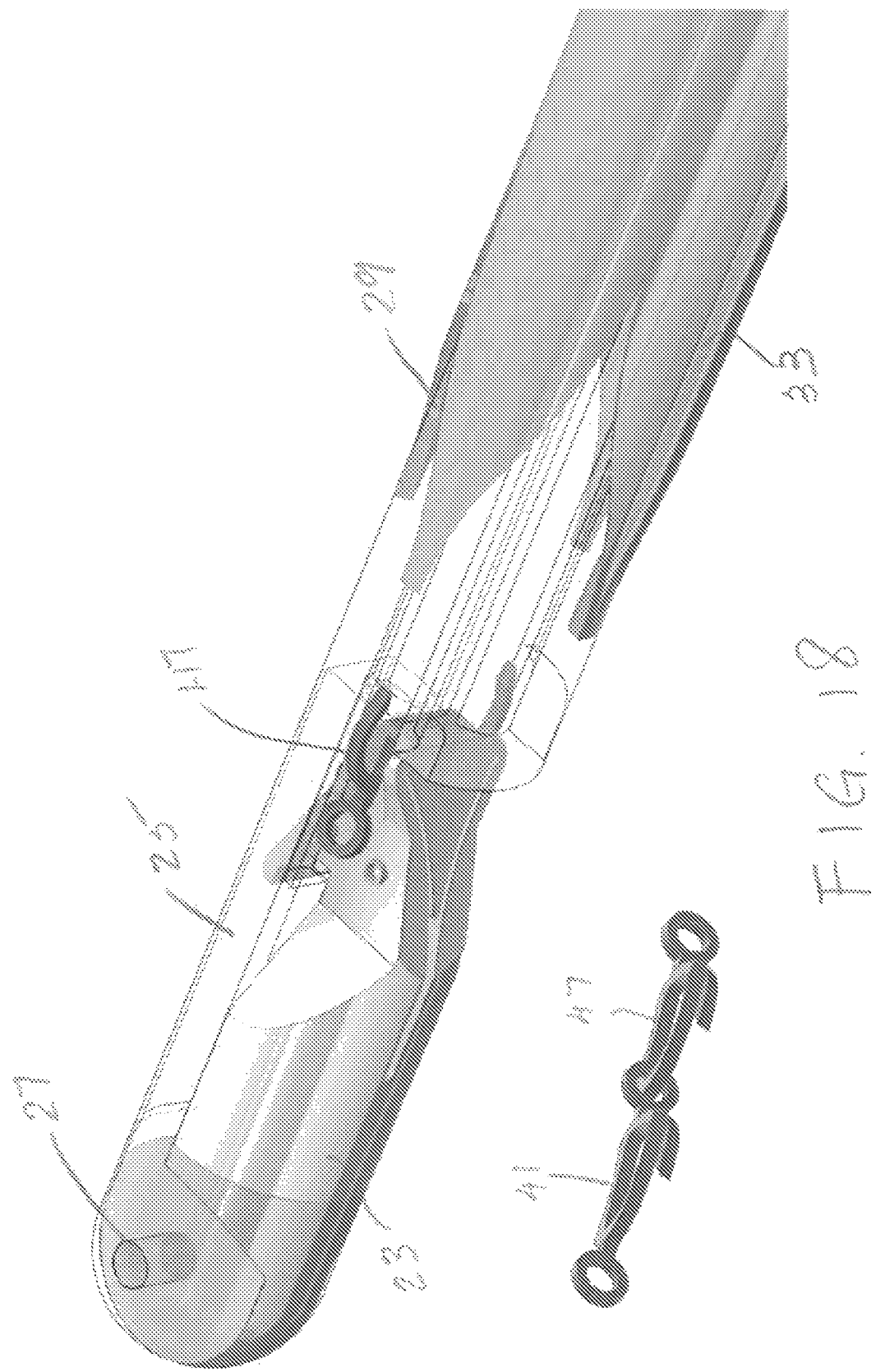
FIG. 18 is a view having the orientation of FIG. 11 showing the stapling head reloaded with a staple oriented so that its lateral ring lies in the opposite orientation to that shown in FIGS. 11-14.

FIG. 18 shows the stapling head 23 having been returned to juxtaposition with the body part 25 at the distal end of the barrel and loaded with another staple 47. In FIG. 18, the staple is oriented at 180° from the staple 47 carried in the stapling head in FIG. 14. Thus, the staple 47 was loaded into the stapling head 23 from the magazine 43 after it had been rotated 180° so that the ring of the staple is attached to the leg on the opposite side compared to that shown in FIGS. 12 and 13.

Figure 19:
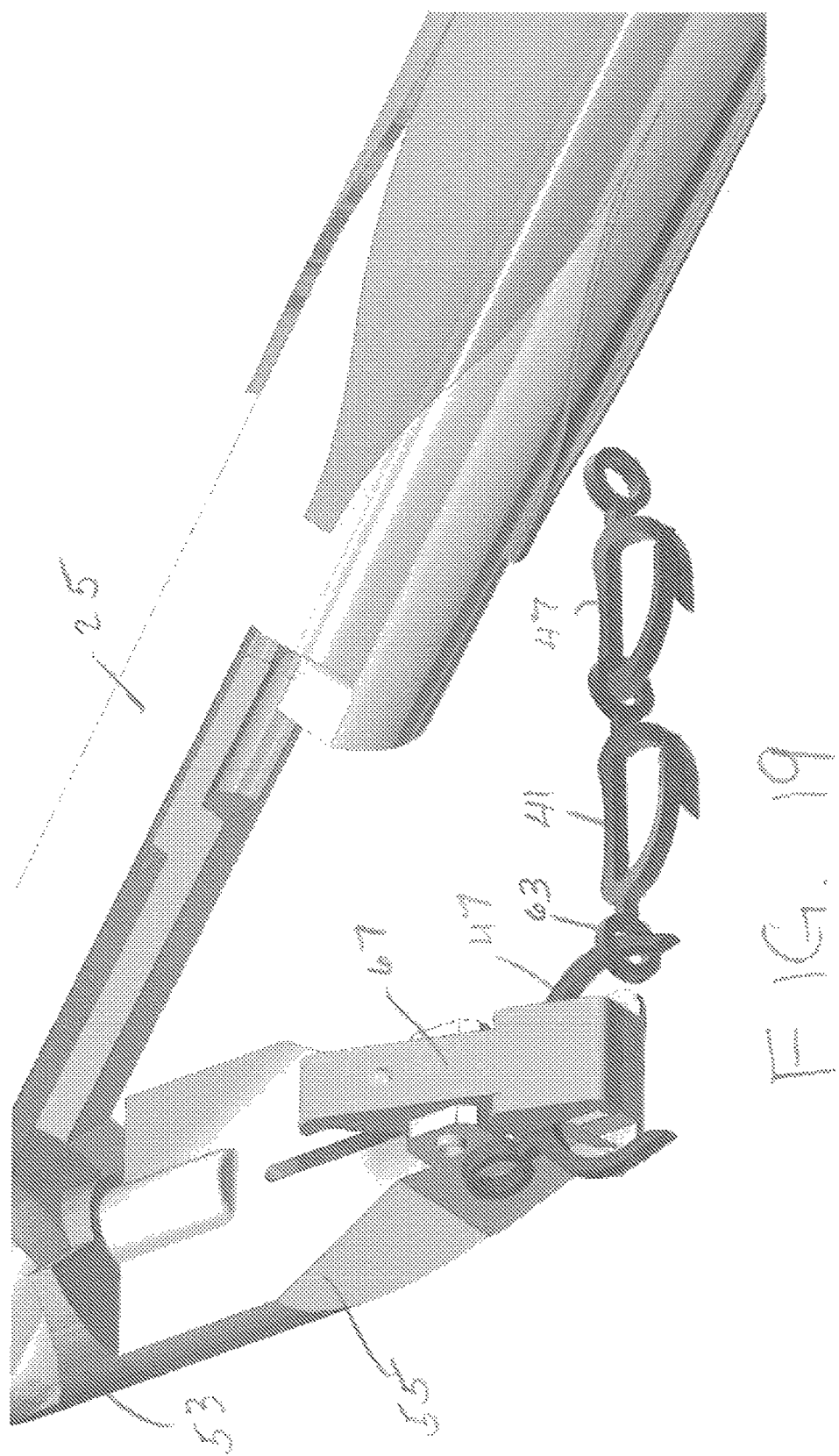
FIG. 19 is a view similar to FIG. 16 showing the staple being implanted with its leg passing through the ring on the left hand side of the original implanted staple.
Figure 20:
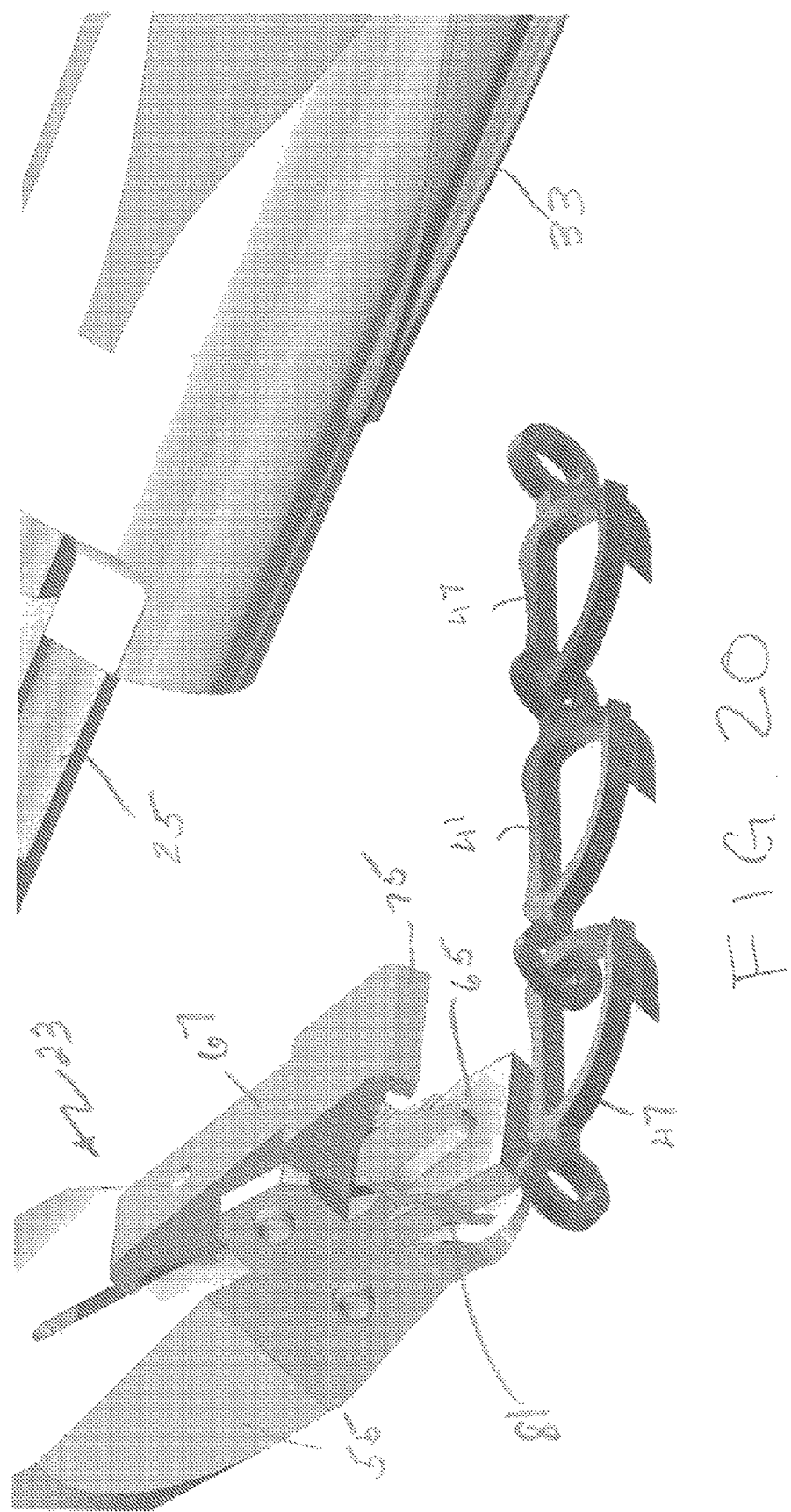
FIG. 20 is a view similar to FIG. 17 showing the $3^{rd}$ staple having been implanted and the stapling head withdrawn slightly.
Figure 21:
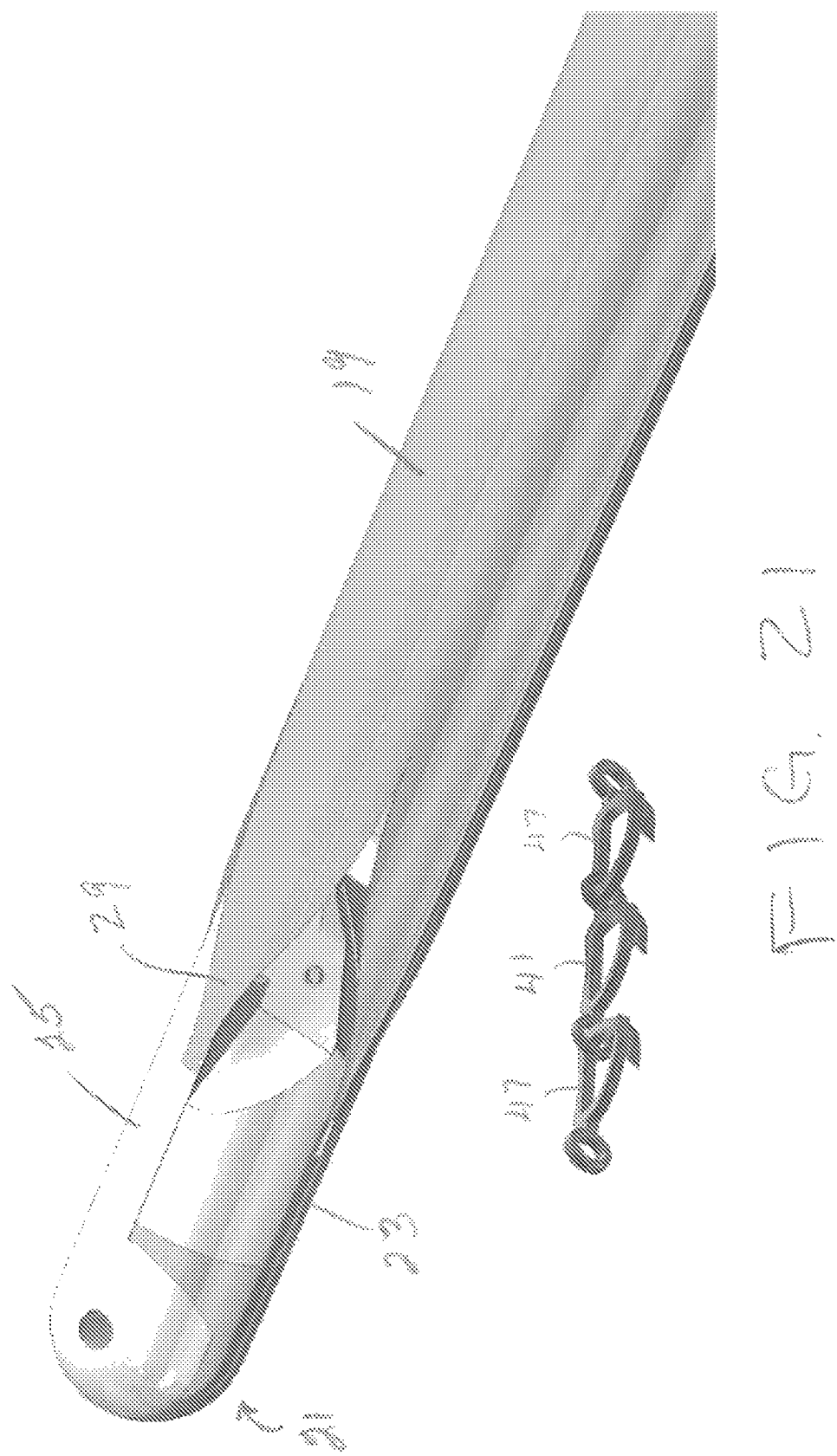
FIG. 21 is a view showing the stapling head having been pivoted back to the at rest position following implantation and the relative retraction of the stapling device distal end of the barrel to a location partially within the sheath.

FIG. 19 depicts the stapler 11 being manipulated by the surgeon so that a leg of the staple 47 protrudes through the ring 63 on the left hand side of the initially implanted staple 41 and ready to be implanted in the heart valve annulus. FIG. 20 shows the completion of the implantation and the slight removal of the stapling head 23; it provides a good view of the holder region 65 where the initial M-shaped staple is received and also shows the track 81 along which a part of the former mechanism 71 moves as it deforms the M-shaped staple to the final implanted shape. Finally, FIG. 21 shows the stapling head 23 having been moved to its juxtaposed, at rest position, and after initial proximal withdrawal movement of the barrel. As a result, the flanged sheath or introducer 19 is beginning the encasement of the stapling head preparatory to extracting the distal end of the stapler from between the leaflets of the mitral valve.

The surgical stapler 11, as indicated hereinbefore, can be adapted for a variety of endoscopic uses; the concept of being able to implant a staple with its prongs oriented proximally, i.e. in a direction generally back toward the handle grip of the stapler, and particularly at an angle of about 45° or less to the longitudinal axis of the stapler, is believed to be unique. However, the surgical stapler 11 illustrated in the drawings, which embodies various features of this inventive concept, is particularly designed for effecting annuloplasty of a heart valve, particularly the mitral valve, which is a bi-leaflet valve that is prone to suffer a pathological condition. The particular design of the illustrated surgical stapler 11 is such that providing access for it to a beating heart through its apex into the left ventricle (LV) is advantageous. To prepare for such entry, a guide-wire 34 is usually first inserted in the left ventricle (LV) through a hollow needle passed through the apex; for example, a device such as that disclosed in Published International Application No. WO 2013/027107 may be used. With the guide-wire 34 in place, its proximal end is fed through the tunnel 33 provided in the side wall of the flanged sheath 19 which extends from a location near the pointed tip of the sheath to the opening 35 in the proximal flange 31.

Figure 24:
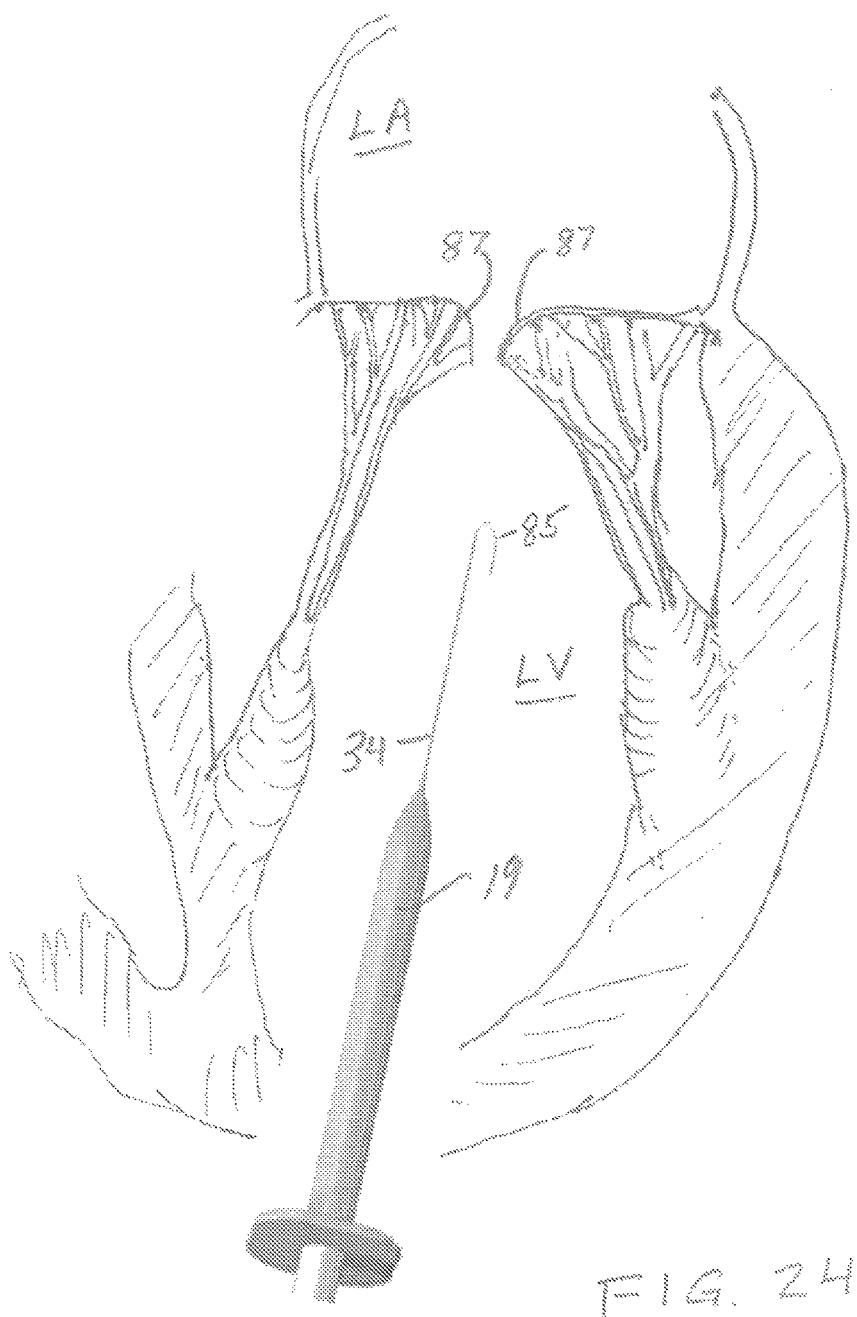
FIG. 24 is a schematic view illustrating the entry of the distal end of the stapler of FIG. 1 through a transapical opening into the left ventricle (LV) of the human heart.
Figure 25:
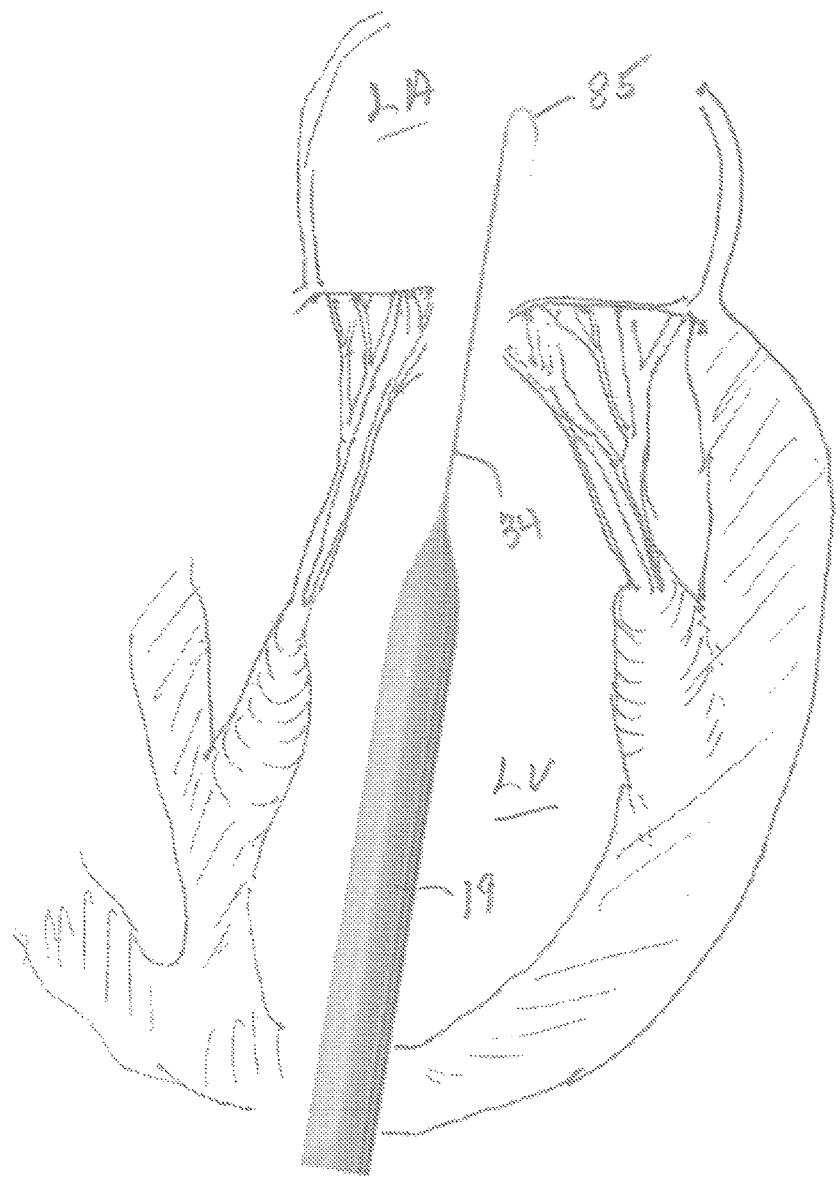
FIG. 25 is a view similar to FIG. 24 where the stapler has been further inserted so the leading guide-wire extends between the leaflets of the mitral valve into the left atrium (LA).

With the sheath 19 in place encasing the stapling device 21 at the distal end of the surgical stapler, it is inserted through the apex of the heart into the left ventricle as schematically shown in FIG. 24. The guide-wire 34 is formed to have a memory such that the distal tip 85 of the wire bends over upon itself to provide a curved forward-facing surface to assure smooth passage between the leaflets 87 of the mitral valve and into the left atrium. Insertion of the stapler so that the curved distal tip 85 of the guide-wire 34 passes into the left atrium (LA) is depicted in FIG. 25. All such movement is guided by X-ray fluoroscopy or preferably by continuous 3D real-time echocardiography.

Figure 26:
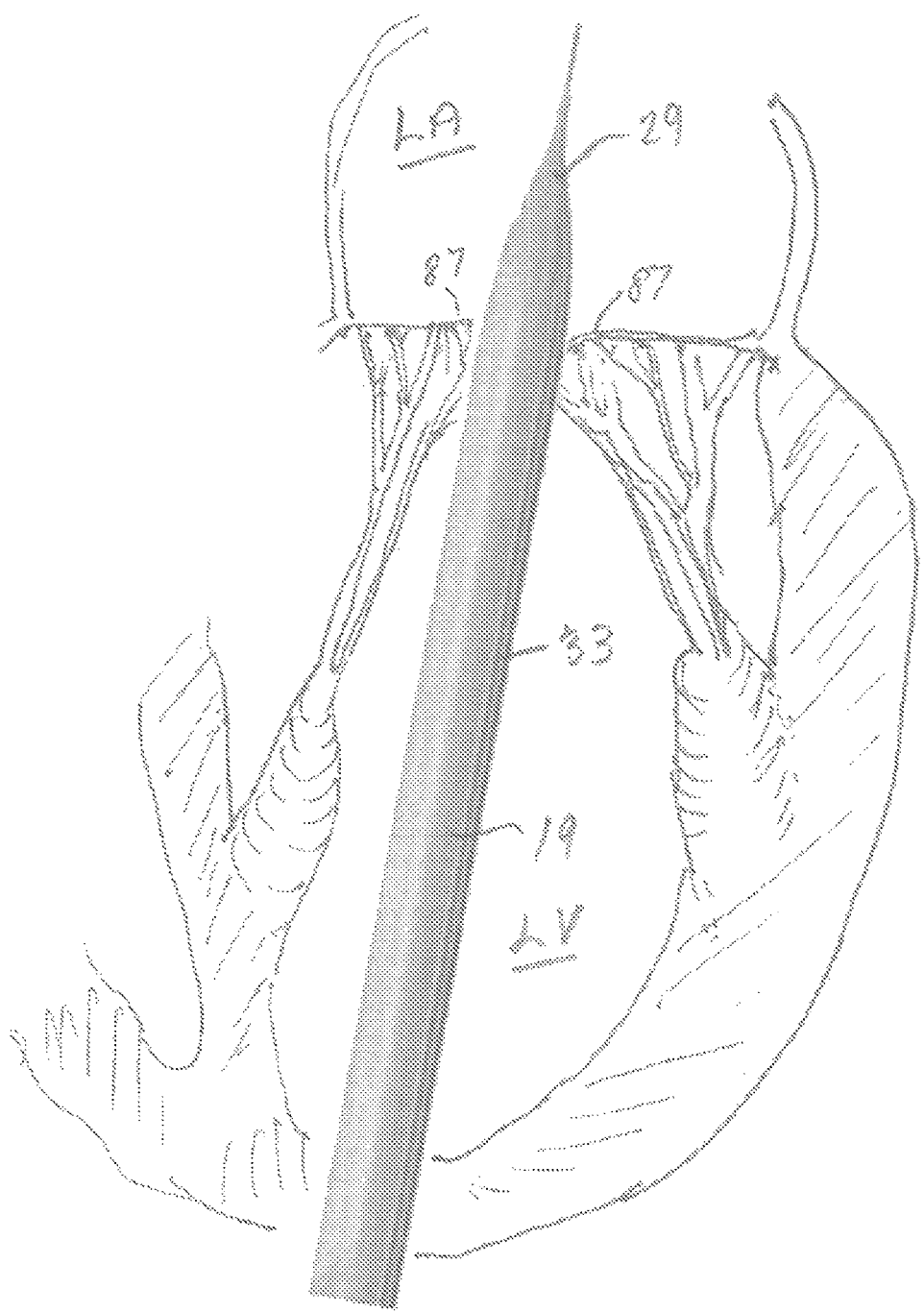
FIG. 26 is a view similar to FIG. 25 where the distal tip of the sheath has been inserted to pass into the LA between the leaflets of the mitral valve and the guide-wire has been withdrawn a substantial distance into a tunnel along the side of the sheath.
Figure 27:
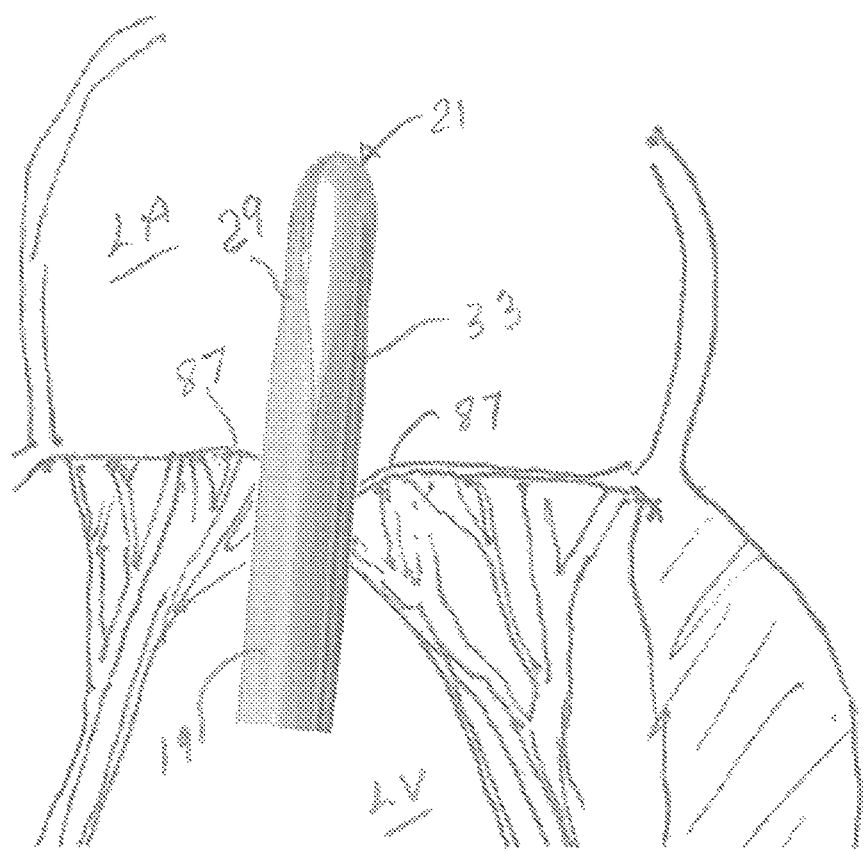
FIG. 27 is an enlarged fragmentary view similar to FIG. 26 wherein the guide-wire has been withdrawn completely into the tunnel and relative movement of the sheath on the barrel of the stapler causes the distal end of the stapler to emerge within the LA.

Next, the stapler 11 is caused to travel along the guide-wire 34, and the pointed tip of the sheath slides between the leaflets 87 to enter the left atrium, as illustrated in FIG. 26. Once the pointed tip 29 of the sheath resides in the left atrium, the guide-wire is withdrawn into the tunnel 33 that extends along the side of the sheath, as shown in FIG. 26 where such partial withdrawal is depicted. With the guide-wire 34 withdrawn, the elongated barrel 17 of the stapler is moved relative to the sheath 19, as shown in FIG. 27 so that the stapling device 21 begins to emerge from the distal end of the opened split tip 29 of the sheath 19.

Figure 28:
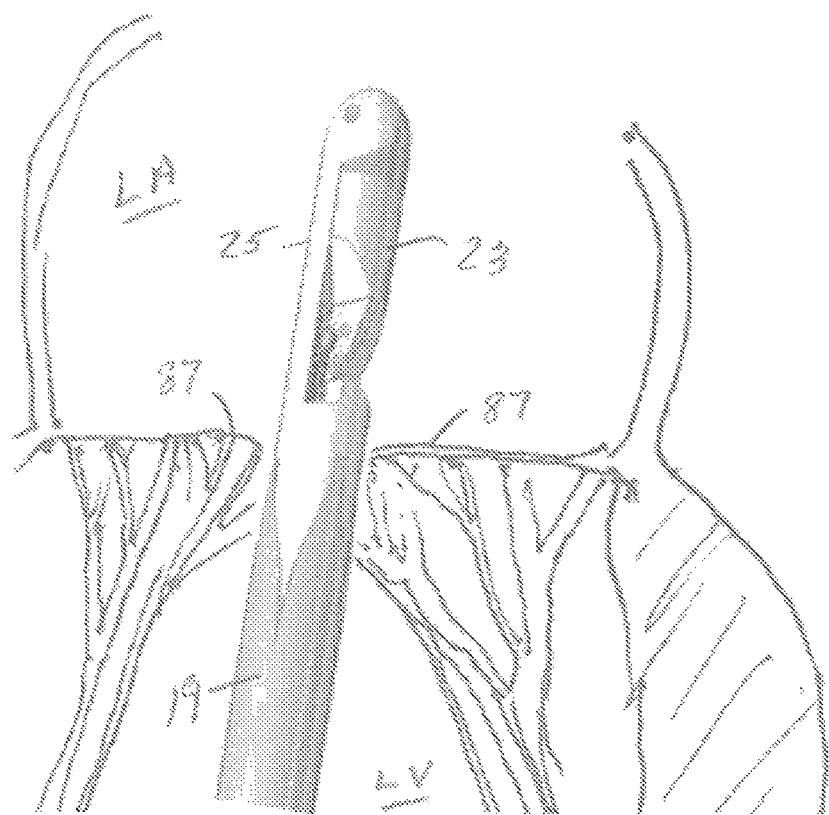
FIG. 28 is a view similar to FIG. 27 showing sufficient relative movement of the sheath along the barrel of the stapler so that the stapling device is totally exposed within the LA.
Figure 29:
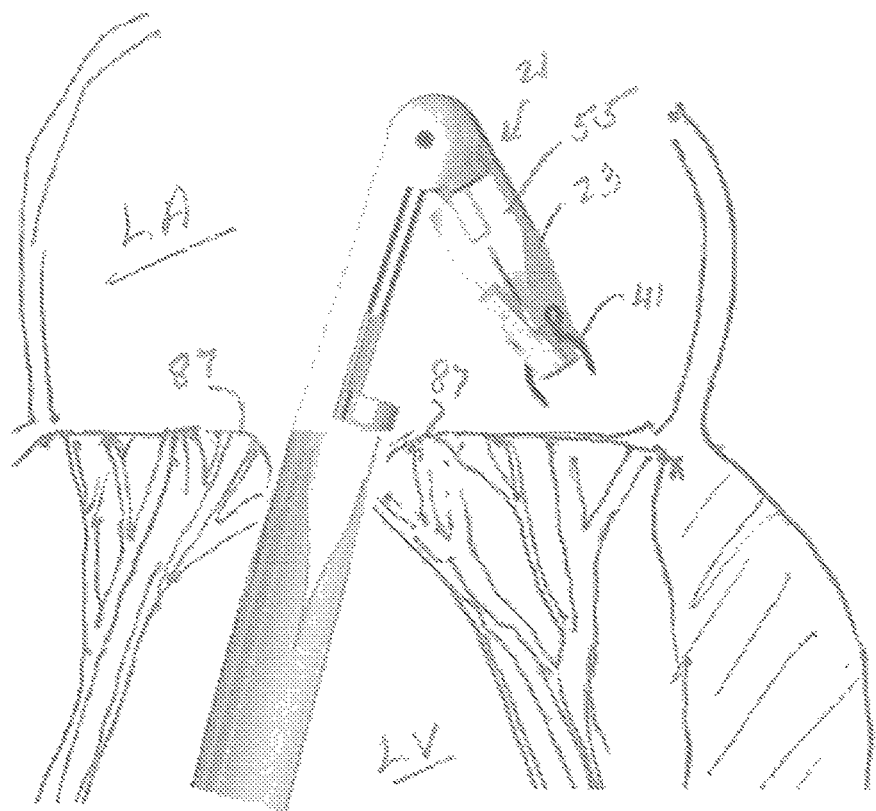
FIG. 29 is a view similar to FIG. 28 showing the stapling head pivoted into an operative position similar to that shown in FIG. 9B.

FIG. 28 shows the flanged sheath 19 withdrawn to a position where the flange 31 would reside at about the stepped portion 39 of the barrel, at which location the stapling device 21 is fully exposed and residing in the left atrium. The tips of the split end 29 of the sheath are located at about the region of the mitral valve leaflets 87. Having reached this location, the stapling head 23 is pivoted away from its at rest juxtaposition with the stapler body 25, and the end portion 55 is rotated so as to position the staple 41, carrying two rings 63, so it is aligned with the mitral valve annulus at about the midpoint of the posterior leaflet. The staple 41 is implanted in this location in the manner earlier described with respect to FIGS. 9B and 10, and the stapling head 23 is then reloaded with one staple 47 at a time from the magazine 43 to create a chain of interconnected staples taking steps as shown in FIGS. 15-20.

Although the implantation of only 3 staples is illustrated, it should be understood that the surgeon will implant a desired number of staples 47 on each side of the central staple 41 along the valve annulus to achieve the desired amount of constriction of the annulus, as described generally in U.S. Pat. No. 8,123,801 and in the '491 patent. The objective of the procedure is to counteract the pathological condition of the mitral valve in order that the leaflets 87 again co-apt to effectively close the valve and prevent, or at least minimize, regurgitation during the pumping stroke of the left ventricle.

In this respect, the surgical stapler 11 is optionally equipped with a crimping mechanism 89 which can effectively change the spacing between the sharpened prongs at the end of the two legs of a staple. The mechanism 89 is located in association with the holder region 65 in the end section 55 of the stapling head 23, and it is designed to apply inward lateral pressure to the exterior lateral surfaces of the stiff legs of the staple to deform them toward each other. For example, the staples may be made from stainless steel or from Co—Cr alloy of comparable stiffness. For instance, the staples 41 and 47 initially loaded in the surgical stapler might be formed so the sharpened tips are spaced from each other about 7.5 mm, and the crimping mechanism 89 can reduce spacing, for example to about 5.5 mm, which might be about the length of the crown connector in its straightened implanted form. The crimping mechanism is operated by a slide 91 located on the grip portion 15 of the handle in the region between the knurled wheels 51 and 57, as best seen perhaps in FIG. 23. Movement of the slide 91 proximally from its at rest position shown in FIG. 23 effects laterally inward bending of the legs of the staple then loaded in the stapling head 23 via linkage that extends through the elongated barrel portion 17 of the handle. This inclusion within the surgical stapler of such a crimping mechanism allows a surgeon to achieve the precise amount of tissue constriction desired with each staple to effect the reshaping of the mitral valve annulus and create an effective annuloplasty, as each staple can be set with its prongs any desired distance between about 7.5 mm and 5.5 mm for example. Although the annuloplasty operation is illustrated and described for a procedure where a first implanted staple 47 having two rings 63 is located in the annulus centrally of the posterior leaflet, it should be understood that a staple could be, if desired, positioned at either end of the desired chain near a trigon and that only staples 47 having a single ring might be used. For example, a chain may be begun near one trigonal region and extend arcuately along the mitral valve annulus in one direction until the desired amount of constriction was obtained by the surgeon.

Moreover, it should be understood that the surgical instrument is such that if, while operation on a beating heart is being performed, it becomes desired to interrupt the staple implantation procedure because the patient ceases to tolerate too long a period of initial incompetence, such can be accommodated to permit revival of the natural blood flow throughout the patient. After implantation of several staples 47 from the magazine, the stapling device can be retracted within the sheath (as shown in FIG. 21) and withdrawn into the left ventricle for a time sufficient to effect such revival. Thereafter, the guide-wire 34 can be again extended from its location in the tunnel 33 and directed between the mitral valve leaflets and into the left atrium as seen in FIG. 25, preparatory to guiding the stapler back into its operative position. If for whatever reason it might be necessary to remove a stapler midway through a surgical procedure, the elongated barrel could be removed, leaving the sheath 19 extending into the LV and the guide-wire 34 in place; the interior unidirectional valve 37 will block the outflow of blood while a substitute stapler is prepared and then inserted along the guide-wire and through the sheath.

Although the invention has been described and illustrated in terms of the best mode presently understood by the inventors to perform such an annuloplasty, it should be understood that various changes and modifications to the devices illustrated made be made without departing from the scope of the invention, which is defined in the claims appended hereto. Furthermore, various features of the invention are emphasized in the claims that follow.

The invention claimed is:

1. A surgical stapler comprising:
   a control handle having a forward-extending barrel; and
   a stapling device at the distal end of the barrel, the stapling device having a stapling head part, a stapler body part, and a hinge connection therebetween such that the stapling head part is pivotable relative to the barrel, wherein the stapling head part has a holder region, opposite the hinge connection, configured for holding a surgical staple during positioning and implanting the staple, and wherein the proximal end portion of the stapling head part can be pivoted outwardly relative to the barrel to at least about 15° from an at rest position, juxtaposed with the stapler body part, to an active position for implantation of a staple into tissue in a generally proximal direction toward the control handle.

2. The stapler of claim 1 wherein the stapling head part has a base section disposed between the hinge connection and the holder region, and wherein the holder region is rotatable relative to the base section.

3. The stapler of claim 1 which further comprises a magazine configured to containing a plurality of staples within the barrel and positioned to sequentially deliver the staples toward the holder region of the stapling head part when said stapling head part is in its at rest position juxtaposed with the stapler body part.

4. The stapler of claim 1 which further comprises a magazine configured to containing a plurality of staples within the barrel and positioned to sequentially deliver the staples toward the holder region of the stapling head part in a direction parallel to a central axis of said barrel when said stapling head part is in its at rest position juxtaposed with the stapler body part.

5. The stapler of claim 3 wherein the magazine is rotatable 180° about a longitudinal axis thereof.

6. The stapler of claim 1 wherein a sheath having a split distal end slidably surrounds the stapling device and the distal end of the barrel and means is provided for sliding the sheath relative to the barrel.

7. The stapler of claim 1 wherein the stapling head part comprises an anvil and a former configured for pressing a staple against the anvil to implant such surgical staple in a patient's tissue.

8. The stapler of claim 7 wherein the stapling head part further comprises a clamp that includes the anvil, said clamp being located to be moved into juxtaposition with the holder region and secure a staple in a ready position for implantation.

9. The stapler of claim 7 further comprising a pusher for engaging a staple at a distal end of said magazine and delivering such staple into said holder region when the stapling head is in its at rest position juxtaposed with the stapler body part.

10. The stapler of claim 1 wherein the stapling head part can be pivoted outwardly relative to the barrel to at least 80° from the at rest position.

11. The stapler of claim 2 wherein the pivoting of the stapling head part and the rotation of the holder region are operable from the control handle.

12. The stapler of claim 1, for use with staples having a pair of legs, which further comprises a crimping mechanism configured for changing the spacing between the two legs of a staple from an initial spacing within the stapler before implantation of such staple into a patient's tissue.

13. The stapler of claim 3 further comprising a withdrawal and delivery mechanism actuated by a lever of said the handle, the movement of which lever being configured to deliver a staple residing at the most distal location in the magazine into said holder region and simultaneously load a spring within said end section that subsequently powers said former, said former being designed to press an undersurface of a crown connector of the staple held in the stapling head against the anvil to cause its legs to move forward and toward each other, implanting the staple in a patient's tissue.

14. The stapler of claim 1 wherein said stapling head part contains a sensor that detects whether both prongs at the ends of said staple legs are penetrating into heart valve tissue and wherein said control handle contains a trigger mechanism for implanting a staple held in the stapling head part and wherein said stapler further comprises an interconnection between said sensor and said trigger mechanism that allows operation of said trigger mechanism only when said sensor detects that both prongs of a staple are symmetrically penetrating into the tissue.

15. The stapler of claim 14 wherein said trigger mechanism includes two buttons on opposite surfaces of said control handle which are designed for substantially coaxial movement in directions toward each other.

16. A surgical stapler for use with generally M-shaped surgical staples having two legs, the stapler comprising:
a control handle having a forward-extending barrel having a central axis,
a stapling device at the distal end of said barrel,
said stapling device comprising
a stapler body part,
a stapling head part pivotably hinged to said body part, and
said stapling head part configured to hold a surgical staple and implant such staple in tissue by causing the two legs to move toward each other, after puncturing a patient's tissue, to a secure final position constricting said tissue, and wherein the head part can pivot to at least about 15° from an at rest position, juxtaposed with said body part, to an active position for implantation of a staple into tissue in a generally proximal direction.

17. The stapler of claim 16 which further comprises a magazine for containing a plurality of generally M-shaped surgical staples in said barrel, and
mechanism which can withdraw one of the surgical staples from said magazine and deliver such into said stapling head part at a time when said stapling head part is pivoted into its rest position.

18. A surgical stapler which comprises:
a handle having a forward-extending barrel,
a stapling device at the distal end of said barrel,
said stapling device comprising
a stapler body part, and
a stapling head part pivotably hinged to said stapler body part, said stapling head part configured to hold a surgical staple of the type having two legs
with prongs at respective ends and implant such staple in tissue by causing said two legs to move toward each other, after puncturing a patient's tissue, to a secure final position constricting said tissue,
a magazine in said barrel configured to contain a plurality of surgical staples,
mechanism which can withdraw one of the surgical staples from said magazine and deliver such, with its prongs pointed in the direction of said handle, into said stapling head part at a time when said stapling head part is in an at rest position juxtaposed with said stapler body part, and
said stapling head part being pivotable to at least about 15° from its at rest position to an active position for implantation of the staple into tissue in a generally proximal direction.

19. The surgical stapler of claim 18 wherein said stapling head part is rigid and is hinged at a pivot point which is distal of an end portion configured for holding a staple when it is delivered to said stapling head and when it is implanted into a patient's tissue.

20. A method of repairing a patient's leaking mitral valve, which method comprises the steps of:
(a) inserting an endoscopic surgical stapler, having a handle and a stapling head part, which carries a surgical staple with its prongs oriented in a direction pointing toward the handle disposed, in folded condition with said elongated body, into the left ventricle of a patient's heart through a transapical passageway,
(b) moving said stapler through the valve opening between the leaflets of the mitral valve into the left atrium,
(c) unfolding said stapler to expose the stapling head part,
(d) implanting said staple into the valve annulus adjacent the posterior leaflet with its prongs still oriented in a direction generally toward the handle, whereby the tissue is constricted where the staple is implanted,
(e) refolding said stapler and reloading another staple into said stapling head part,
(f) unfolding the reloaded stapler and implanting another staple adjacent the implanted staple,
(g) repeating steps (e) and (f) to adequately change the shape of the mitral valve annulus so as to effect improved closing of the mitral valve, and
(h) refolding said stapler and withdrawing it from the heart of the patient.

* * * * *